(12) United States Patent
Kinnunen et al.

(10) Patent No.: US 11,793,454 B2
(45) Date of Patent: Oct. 24, 2023

(54) METHOD AND SYSTEM FOR PROVIDING FEEDBACK TO USER FOR IMPROVING PERFORMANCE LEVEL MANAGEMENT THEREOF

(71) Applicant: OURA HEALTH OY, Oulu (FI)

(72) Inventors: Hannu Olavi Kinnunen, Oulu (FI); Heidi Jurvelin, Oulu (FI); Marko Petteri Lahtela, Jääli (FI)

(73) Assignee: Oura Health Oy, Oulu (FI)

( * ) Notice: Subject to any disclaimer, the term of this patent is extended or adjusted under 35 U.S.C. 154(b) by 327 days.

(21) Appl. No.: 16/909,202

(22) Filed: Jun. 23, 2020

(65) Prior Publication Data

US 2021/0007658 A1  Jan. 14, 2021

Related U.S. Application Data

(63) Continuation-in-part of application No. 15/235,641, filed on Aug. 12, 2016, now abandoned.
(Continued)

(51) Int. Cl.
| | |
|---|---|
| *A61B 5/00* | (2006.01) |
| *A61B 5/11* | (2006.01) |
| *A61B 5/01* | (2006.01) |
| *A61B 5/024* | (2006.01) |
| *A61B 5/08* | (2006.01) |
(Continued)

(52) U.S. Cl.
CPC .......... *A61B 5/4812* (2013.01); *A61B 5/0024* (2013.01); *A61B 5/01* (2013.01); *A61B 5/0205* (2013.01); *A61B 5/02405* (2013.01); *A61B 5/02438* (2013.01); *A61B 5/08* (2013.01); *A61B 5/11* (2013.01); *A61B 5/6801* (2013.01);
(Continued)

(58) Field of Classification Search
CPC ..... A61B 5/4857; A61B 5/746; A61B 5/7246; A61B 5/6801; A61B 5/11
See application file for complete search history.

(56) References Cited

U.S. PATENT DOCUMENTS

| | | | |
|---|---|---|---|
| 2011/0015495 A1* | 1/2011 | Dothie | A47C 31/123 600/300 |
| 2014/0052220 A1* | 2/2014 | Pedersen | A61N 5/0618 607/88 |

(Continued)

*Primary Examiner* — Lynsey C Eiseman
*Assistant Examiner* — Amanda L Steinberg
(74) *Attorney, Agent, or Firm* — Holland & Hart LLP

(57) ABSTRACT

A method includes collecting a set of user information, determining a user current performance by: determining a sleep score or debt, measuring the user's previous physical activity, heart rate, or body temperature, calculating weights for the sleep score and the sleep debt, the measured previous physical activity, heart rate, or body temperature, calculating a weighted sum of the weighted sleep score, the weighted sleep debt, the weighted user's previous physical activity, weighted heart rate, or weighted body temperature, setting a user target level of performance, measuring a circadian rhythm and a user's duration of sleep or sleep cycle, comparing the circadian rhythm, the duration of sleep or sleep cycle, the current performance level, and current time zone information over days to determine a separate user performance level, comparing the target level of performance to the separate user performance level, and providing an alert and feedback user related to the comparison.

11 Claims, 4 Drawing Sheets

Related U.S. Application Data

(60) Provisional application No. 62/205,112, filed on Aug. 14, 2015.

(51) Int. Cl.
*A61B 5/0205* (2006.01)
*G16H 20/70* (2018.01)

(52) U.S. Cl.
CPC .............. *A61B 5/7246* (2013.01); *A61B 5/746* (2013.01); *G16H 20/70* (2018.01); *A61B 5/4857* (2013.01)

(56) References Cited

U.S. PATENT DOCUMENTS

2016/0270718 A1* 9/2016 Heneghan .......... A61M 16/0069
2018/0289314 A1* 10/2018 Reifman ............... A61B 5/1118

* cited by examiner

METHOD AND SYSTEM FOR PROVIDING FEEDBACK TO USER FOR IMPROVING PERFORMANCE LEVEL MANAGEMENT THEREOF

This is a continuation in part of U.S. patent application Ser. No. 15/235,641, filed on 12 Aug. 2016, incorporated by reference herein in its entirety.

TECHNICAL FIELD

The present disclosure relates generally to analysing and processing data related to the physiological state of an individual, and, more specifically, to a method and a system for providing feedback to a user for improving performance level management thereof.

BACKGROUND

An individual is subjected to various kinds of stresses in a day to day life. For example, an individual may be subjected to stress due to physical loads (such as travelling between places of different time zones, performing more physical activity and the like) and mental loads (such as inadequate sleep, stress and the like). Further, if such stresses are not managed or handled efficiently by the individual, he or she may be subjected to health issues. For example, it may cause health issues such as backache, spine problems and headache, hinder concentration and impair motivation, and affect appetite leading to weight gain. This in turn may affect the performance level of the individual in respect to ability to attain to a routine job or start a day. Therefore, it is important to analyse how an individual handles and/or recovers from such stresses for managing performance level thereof.

Conventionally, there are many electronically wearable devices that may help a user to guide for recovering from the stress and thereby improve his performance level. Generally, such devices calculate a score, depending on which it guides the individual to take appropriate actions. Typically, the score may be calculated based on a variety of physiological data (or parameters) associated with the user, such as Epworth Sleepiness Scale (ESS) for determining sleepiness, Holmes and Rahe Stress Scale for determining stress level and the like. Further, the calculation of the score may be based on the user input, for example, answers to question related to physiological aspects. Moreover, the question may be associated with permanent answers, such as gender; alternatively the question may be associated with temporary answers (changing with time) such as age, biological data and the like.

However, such devices do not take into account personal variances, targets and preferences of the individual which could impact the results. For example, such devices do not take into consideration travel information of the individual (i.e. non-physiological information), such as when the user is travelling between places having different time zones, which may cause change (or disturbance) in a biological clock of the user. Further, such devices do not analyse data, associated with physiological parameters of the individual, in detail. For example, such devices do not consider the individual's historical physiological data. Additionally, such devices are not capable of providing appropriate feedback and instruction (or guidance) that may help the individual to efficiently recover from physical and mental load (or stress) to improve his or her performance level. Additionally, such devices do not take into consideration the user's preferences, such as morningness, eveningness, having a baby, preference to adapt to time difference by delaying or advancing their rhythm, and so on. Additionally, such devices do not follow if the user is following the guidance and how well the targets are reached and then modify and change such guides which do not work or strengthen such guides which work well.

Therefore, in light of the foregoing discussion, there exists a need to overcome the aforementioned drawbacks of the conventional devices for improving performance level management for a user. Especially the problem is to obtain a useful metrics to give useful feedback and to guide a user automatically by a device and program so that the recovering can be realistic, safe and adapted to personal preferences.

SUMMARY

The present disclosure seeks to provide a method for providing feedback to a user for improving performance level management. The present disclosure also seeks to provide a system for providing feedback to a user for improving performance level management. The present invention aims at at least partially solving the problems encountered in prior art, and to provide a method and system for providing feedback that are both easy and reliable to use.

In one aspect, an embodiment of present invention provides a method for providing feedback to a user for improving performance level management, comprising steps of:
  collecting a first set of information from the user;
  determining a current performance level of the user by:
  using a wearable electronic device to determine a sleep score and a sleep debt, and measure one or more of the user's previous physical activity, heart rate, or body temperature;
  calculating weights for the sleep score and the sleep debt, and for the measured one or more of the user's previous physical activity, heart rate, or body temperature; and
  calculating a weighted sum of the weighted sleep score and weighted sleep debt, and the one or more of the weighted user's previous physical activity, weighted heart rate, or weighted body temperature;
  setting a target level of performance of the user;
  measuring by sensors of the wearable electronic device, at least one parameter that describes a circadian rhythm and at least one parameter that describes a duration of sleep or sleep cycle of the user;
  comparing the at least one parameter that describes a circadian rhythm, the at least one parameter that describes a duration of sleep or sleep cycle of the user, the current performance level, and current time zone information measured over a plurality of days to determine a separately determined performance level of the user;
  comparing the target level of performance of the user to the separately determined performance level of the user; and
    providing an alert and feedback to the user related to the comparison of the target level of performance and the separately determined performance level;
  wherein the feedback comprises instructions to the user to change the duration of sleep or the sleep cycle of the user to achieve the target level of performance and the feedback is based on whether the user is a morning or evening person.

In another aspect, an embodiment of the present disclosure provides a system for providing feedback to a user for improving performance level management. The system comprises:

a wearable electronic device configured to be worn by the user and comprising sensors for measuring circadian rhythm and duration of sleep;

a mobile communication device configured to communicate with the wearable electronic device; and a server configured to communicate with the mobile communication device, the server being configured to:

collect a first set of information from the user, determine a current performance level of the user by:

use a wearable electronic device to determine a sleep score and a sleep debt, and measure one or more of the user's previous physical activity, heart rate, or body temperature;

calculate weights for the sleep score and the sleep debt, and for the measured one or more of the user's previous physical activity, heart rate, or body temperature; and calculate a weighted sum of the weighted sleep score and weighted sleep debt, and the one or more of the weighted user's previous physical activity, weighted heart rate, or weighted body temperature;

set a target level of performance of the user, compare the measured circadian rhythm, the measured duration of sleep, the current performance level and current time zone information measured over a plurality of days to determine a separately determined performance level of the user, compare the separately determined performance level to the target level of performance, and provide an alert and feedback, on the mobile communication device, to the user when the separately determined performance level is below the target level of performance, wherein the feedback comprises instructions to the user to change the duration of sleep or the sleep cycle of the user to achieve the target level of performance.

In yet another aspect, an embodiment of the present disclosure provides a method for providing feedback to a user for improving performance level management, the method comprising:

collecting a first set of information from the user;

determining a current performance level of the user by:

using a wearable electronic device to determine a sleep score and a sleep debt, and measure one or more of the user's previous physical activity, heart rate, or body temperature;

calculating weights for the sleep score and the sleep debt, and for the measured one or more of the user's previous physical activity, heart rate, or body temperature; and calculating a weighted sum of the weighted sleep score and weighted sleep debt, and the one or more of the weighted user's previous physical activity, weighted heart rate, or weighted body temperature;

setting a target level of performance of the user;

measuring by sensors of the wearable electronic device, at least one parameter that describes a circadian rhythm and at least one parameter that describes a duration of sleep or sleep cycle of the user, wherein the duration of sleep or sleep cycle is below the user's personal average;

comparing the at least one parameter that describes a circadian rhythm, the at least one parameter that describes a duration of sleep or sleep cycle of the user, the current performance level, and current time zone information measured over a plurality of days to determine a separately determined performance level of the user;

comparing the target level of performance of the user to the separately determined performance level of the user; and providing an alert and feedback to the user when the separately determined performance level is below the target level of performance because the duration of sleep or sleep cycle is below the user's personal average;

wherein the feedback comprises instructions to the user to change the duration of sleep or the sleep cycle of the user to achieve the target level of performance and the feedback is based on whether the user is a morning or evening person.

In a further aspect, an embodiment of the present disclosure provides a method for providing feedback to a user for improving performance level management, the method comprising:

collecting from the user a first set of information comprising one or more of travel information, current time zone information, the user's calendar, working schedule and holidays;

determining a current performance level of the user by:

using a wearable electronic device to determine a sleep score and a sleep debt, and measure one or more of the user's previous physical activity, heart rate, or body temperature;

calculating weights for the sleep score and the sleep debt, and for the measured one or more of the user's previous physical activity, heart rate, or body temperature; and calculating a weighted sum of the weighted sleep score and weighted sleep debt, and the one or more of the weighted user's previous physical activity, weighted heart rate, or weighted body temperature;

setting a target level of performance of the user;

measuring by sensors of the wearable electronic device, at least one parameter that describes a circadian rhythm and at least one parameter that describes a duration of sleep or sleep cycle of the user;

comparing the at least one parameter that describes a circadian rhythm, the at least one parameter that describes a duration of sleep or sleep cycle of the user, the current performance level, and current time zone information measured over a plurality of days to determine a separately determined performance level of the user;

comparing the target level of performance of the user to the separately determined performance level of the user; and providing an alert and feedback to the user when the separately determined performance level is below the target level of performance because of jet lag;

wherein the feedback comprises instructions from the wearable device to the user to change the duration of sleep or the sleep cycle of the user to achieve the target level of performance.

Embodiments of the present disclosure substantially eliminate or at least partially address the aforementioned problems in the prior art, and enables improvement of performance level management for a user.

Additional aspects, advantages, features and objects of the present disclosure would be made apparent from the drawings and the detailed description of the illustrative embodiments construed in conjunction with the appended claims that follow.

It will be appreciated that features of the present disclosure are susceptible to being combined in various combinations without departing from the scope of the present disclosure as defined by the appended claims.

BRIEF DESCRIPTION OF THE DRAWINGS

The summary above, as well as the following detailed description of illustrative embodiments, is better understood when read in conjunction with the appended drawings. For the purpose of illustrating the present disclosure, exemplary constructions of the disclosure are shown in the drawings.

However, the present disclosure is not limited to specific methods and instrumentalities disclosed herein. Moreover, those in the art will understand that the drawings are not to scale. Wherever possible, like elements have been indicated by identical numbers.

Figure 1:
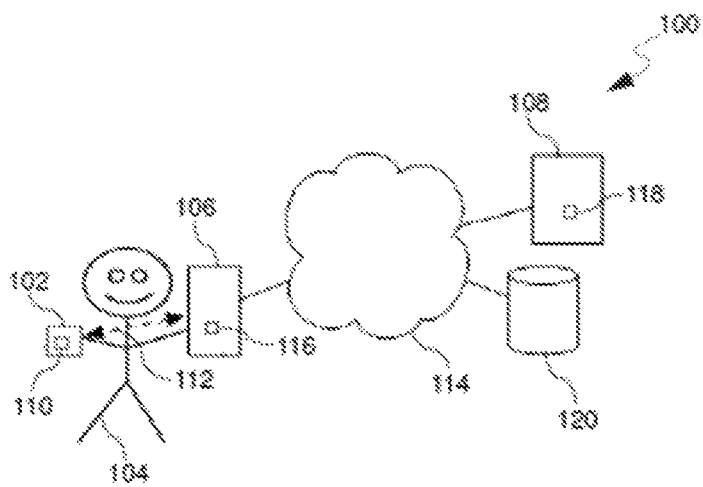
Figure 2:
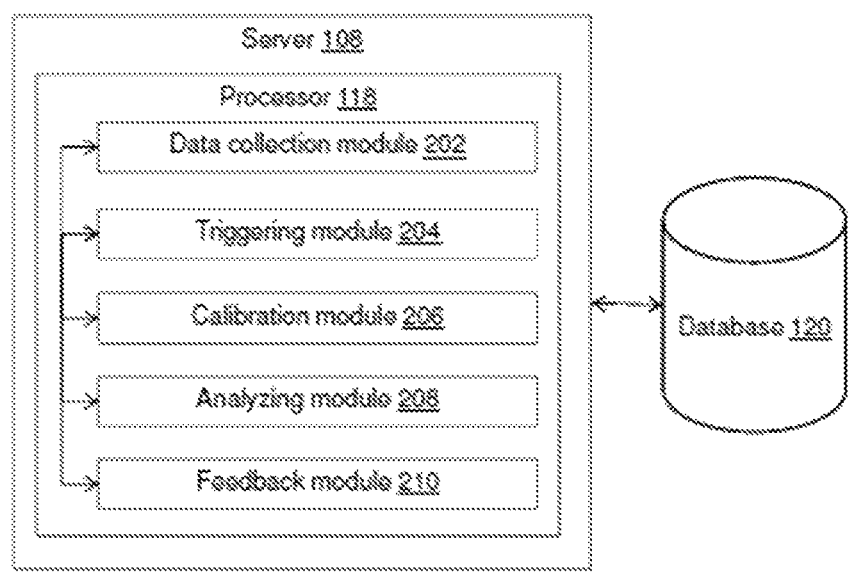
Figure 3:
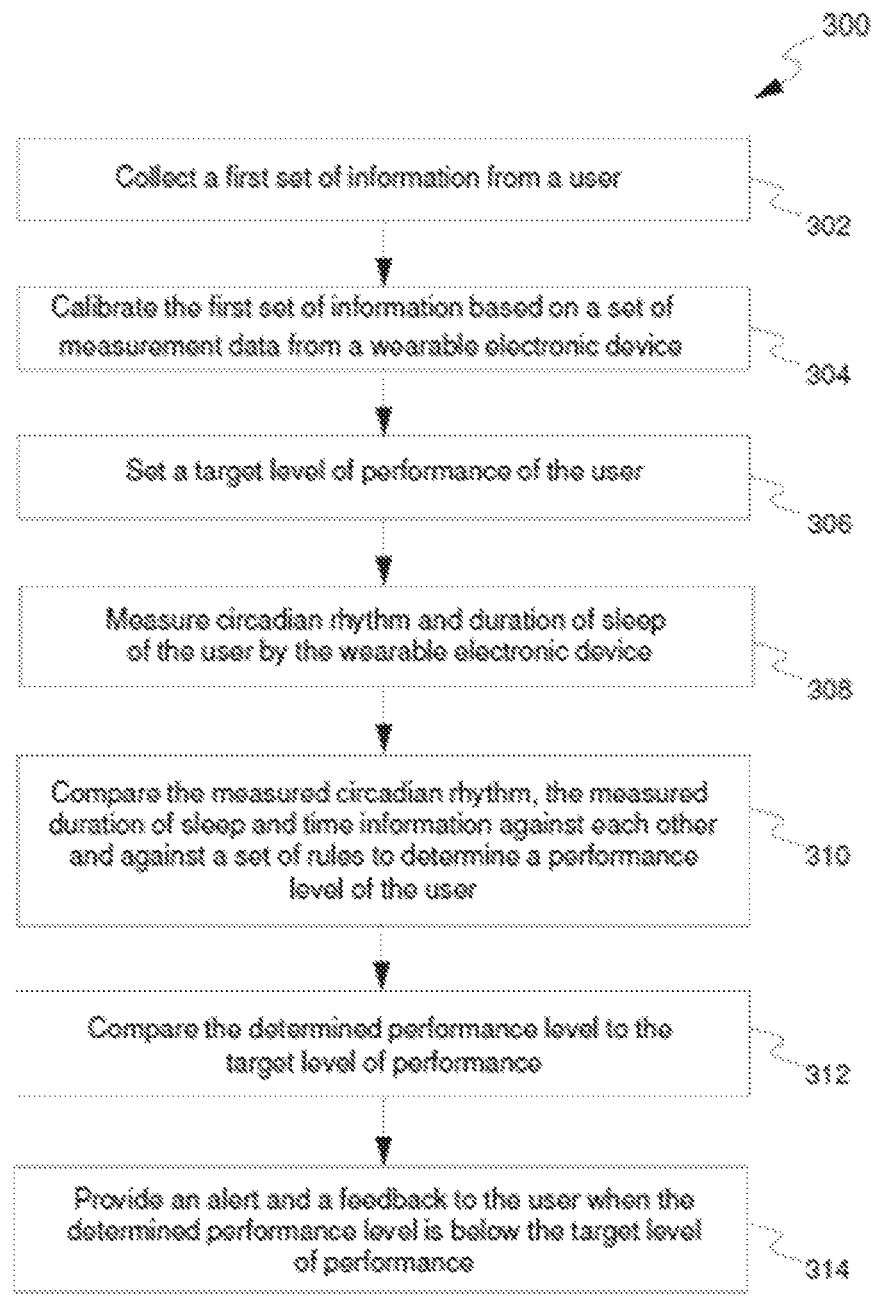

Embodiments of the present disclosure will now be described, by way of example only, with reference to the following diagrams wherein:

FIG. 1 is a block diagram illustrating a system for providing feedback to a user for improving performance level management thereof, in accordance with an embodiment of the present disclosure;

FIG. 2 is a block diagram illustrating various modules of a server of the system of FIG. 1, in accordance with an embodiment of the present disclosure; and FIG. 3 is an illustration of steps of a method for providing feedback to a user for improving performance level management thereof, in accordance with an embodiment of the present disclosure.

Figure 4:
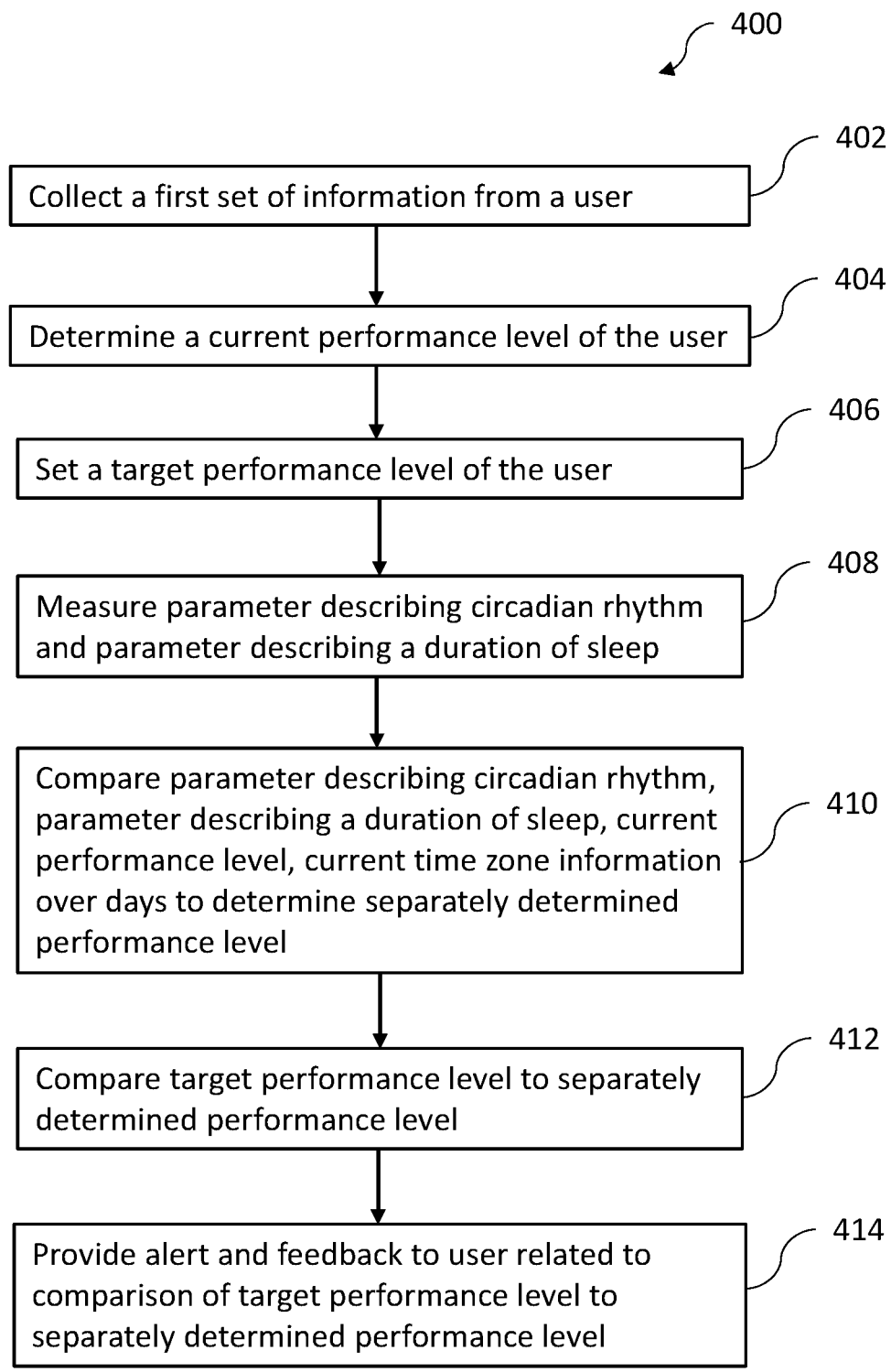

FIG. 4 is an illustration of steps of an additional method for providing feedback to a user for improving performance level management thereof, in accordance with an embodiment of the present disclosure.

Figure 5:
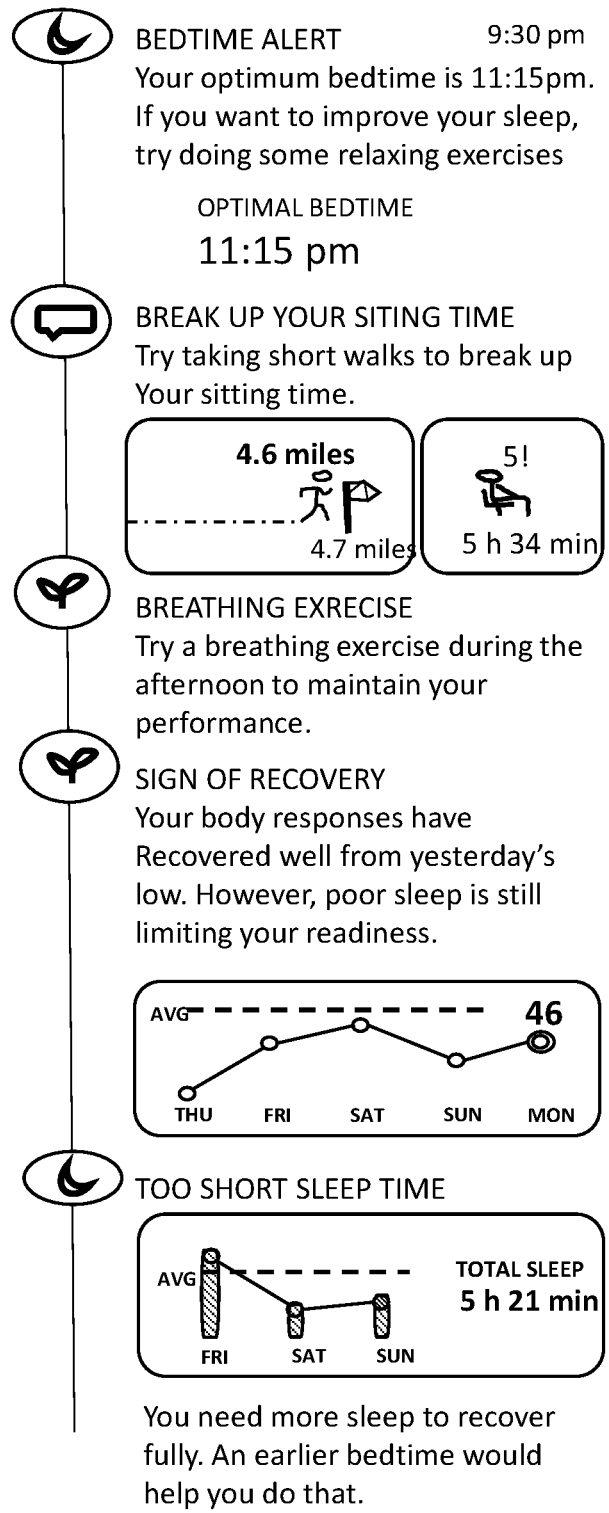

FIG. 5 is an illustration of an exemplary user interface for providing feedback to the user in a system and using a method incorporating aspects of the disclosed embodiments.

In the accompanying drawings, an underlined number is employed to represent an item over which the underlined number is positioned or an item to which the underlined number is adjacent. A non-underlined number relates to an item identified by a line linking the non-underlined number to the item. When a number is non-underlined and accompanied by an associated arrow, the non-underlined number is used to identify a general item at which the arrow is pointing.

DETAILED DESCRIPTION OF EMBODIMENTS

The following detailed description illustrates embodiments of the present disclosure and ways in which they can be implemented. Although some modes of carrying out the present disclosure have been disclosed, those skilled in the art would recognize that other embodiments for carrying out or practicing the present disclosure are also possible.

In one aspect, an embodiment of present invention provides a method for providing feedback to a user for improving performance level management, comprising steps of:
collecting a first set of information from the user;
determining a current performance level of the user by:
using a wearable electronic device to determine a sleep score and a sleep debt, and measure one or more of the user's previous physical activity, heart rate, or body temperature;
calculating weights for the sleep score and the sleep debt, and for the measured one or more of the user's previous physical activity, heart rate, or body temperature; and
calculating a weighted sum of the weighted sleep score and weighted sleep debt, and the one or more of the weighted user's previous physical activity, weighted heart rate, or weighted body temperature;
setting a target level of performance of the user;
measuring by sensors of the wearable electronic device, at least one parameter that describes a circadian rhythm and at least one parameter that describes a duration of sleep or sleep cycle of the user;
comparing the at least one parameter that describes a circadian rhythm, the at least one parameter that describes a duration of sleep or sleep cycle of the user, the current performance level, and current time zone information measured over a plurality of days to determine a separately determined performance level of the user;
comparing the target level of performance of the user to the separately determined performance level of the user; and
providing an alert and feedback to the user related to the comparison of the target level of performance and the separately determined performance level;
wherein the feedback comprises instructions to the user to change the duration of sleep or the sleep cycle of the user to achieve the target level of performance and the feedback is based on whether the user is a morning or evening person.

In another aspect, an embodiment of the present disclosure provides a system for providing feedback to a user for improving performance level management. The system comprises:
a wearable electronic device configured to be worn by the user and comprising sensors for measuring circadian rhythm and duration of sleep;
a mobile communication device configured to communicate with the wearable electronic device; and
a server configured to communicate with the mobile communication device, the server being configured to:
collect a first set of information from the user,
determine a current performance level of the user by:
use a wearable electronic device to determine a sleep score and a sleep debt, and measure one or more of the user's previous physical activity, heart rate, or body temperature;
calculate weights for the sleep score and the sleep debt, and for the measured one or more of the user's previous physical activity, heart rate, or body temperature; and
calculate a weighted sum of the weighted sleep score and weighted sleep debt, and the one or more of the weighted user's previous physical activity, weighted heart rate, or weighted body temperature;
set a target level of performance of the user,
compare the measured circadian rhythm, the measured duration of sleep, the current performance level and current time zone information measured over a plurality of days to determine a separately determined performance level of the user,
compare the separately determined performance level to the target level of performance, and
provide an alert and feedback, on the mobile communication device, to the user when the separately determined performance level is below the target level of performance, wherein the feedback comprises instructions to the user to change the duration of sleep or the sleep cycle of the user to achieve the target level of performance.

In yet another aspect, an embodiment of the present disclosure provides a method for providing feedback to a user for improving performance level management, the method comprising:
collecting a first set of information from the user;
determining a current performance level of the user by:
using a wearable electronic device to determine a sleep score and a sleep debt, and measure one or more of the user's previous physical activity, heart rate, or body temperature;
calculating weights for the sleep score and the sleep debt, and for the measured one or more of the user's previous physical activity, heart rate, or body temperature; and
calculating a weighted sum of the weighted sleep score and weighted sleep debt, and the one or more of the weighted user's previous physical activity, weighted heart rate, or weighted body temperature;

setting a target level of performance of the user;

measuring by sensors of the wearable electronic device, at least one parameter that describes a circadian rhythm and at least one parameter that describes a duration of sleep or sleep cycle of the user, wherein the duration of sleep or sleep cycle is below the user's personal average;

comparing the at least one parameter that describes a circadian rhythm, the at least one parameter that describes a duration of sleep or sleep cycle of the user, the current performance level, and current time zone information measured over a plurality of days to determine a separately determined performance level of the user;

comparing the target level of performance of the user to the separately determined performance level of the user; and providing an alert and feedback to the user when the separately determined performance level is below the target level of performance because the duration of sleep or sleep cycle is below the user's personal average;

wherein the feedback comprises instructions to the user to change the duration of sleep or the sleep cycle of the user to achieve the target level of performance and the feedback is based on whether the user is a morning or evening person.

In a further aspect, an embodiment of the present disclosure provides a method for providing feedback to a user for improving performance level management, the method comprising:

collecting from the user a first set of information comprising one or more of travel information, current time zone information, the user's calendar, working schedule and holidays;

determining a current performance level of the user by:

using a wearable electronic device to determine a sleep score and a sleep debt, and measure one or more of the user's previous physical activity, heart rate, or body temperature;

calculating weights for the sleep score and the sleep debt, and for the measured one or more of the user's previous physical activity, heart rate, or body temperature; and calculating a weighted sum of the weighted sleep score and weighted sleep debt, and the one or more of the weighted user's previous physical activity, weighted heart rate, or weighted body temperature;

setting a target level of performance of the user;

measuring by sensors of the wearable electronic device, at least one parameter that describes a circadian rhythm and at least one parameter that describes a duration of sleep or sleep cycle of the user;

comparing the at least one parameter that describes a circadian rhythm, the at least one parameter that describes a duration of sleep or sleep cycle of the user, the current performance level, and current time zone information measured over a plurality of days to determine a separately determined performance level of the user;

comparing the target level of performance of the user to the separately determined performance level of the user; and providing an alert and feedback to the user when the separately determined performance level is below the target level of performance because of jet lag;

wherein the feedback comprises instructions from the wearable device to the user to change the duration of sleep or the sleep cycle of the user to achieve the target level of performance.

The system of the present disclosure specifically provides feedback to the user for improving performance level management. The term "performance level" used herein is primarily associated with the physiological state of the user, i.e. readiness, capacity, wellness, preparedness or wellbeing of the user, for attending to regular routine jobs and tasks. In an example, the performance level may be the physiological state of the user, i.e. how well and fresh the user is feeling at the moment the user got up from the sleep to start a day. Further, the performance level may be primarily derived from the physiological data (or parameters) measured by the wearable electronic device, i.e. heart-rate-variability, a respiration rate, a sleeping pattern of the user, a hypnogram of the user, the user's stress level and the like. Moreover, the performance level may also include external and internal factors (or aspects) associated with the user to derive (or calculate) the performance level of the user, which is explained herein later. Additionally the term performance can refer to night-time performance meaning good sleeping and recovery abilities, e.g. ability to get enough deep sleep that is associated with secretion of growth hormone, or good sleep efficiency, or feeling refreshed most of the mornings during the week, or day-time performance e.g. learning ability, cognitive and physiological performance.

In an embodiment, the wearable electronic device of the system is a ring configured to be suitably worn on a finger, such as an index finger, of the user. However, it may be evident to those skilled in the art that the system may be associated with other wearable electronic devices, such as a device adapted to be worn on wrist, chest and any suitable body part of the user, from where physiological data of the user can be measured. In such instance, the wearable electronic device may be configured to have a size to be suitably worn on such body parts. According to a further embodiment, the wearable electronic device is as described in PCT/FI2014/000043, which application is hereby incorporated by reference.

In an embodiment, the wearable electronic device is generally configured to collect data about the user. For example, the wearable electronic device may comprise at least one sensor, selected from the group consisting of an accelerometer, a gyroscope and a magnetic field sensor, for measuring the user's movements. Further, the user's heart rate may be measured using a photon (for example infrared) source and a photon detector also arranged on an inner surface of the wearable electronic device. In another embodiment, the wearable electronic device further comprises a sensor comprising a first electrode and a second electrode adapted to measure an electrocardiogram. Additionally, the wearable electronic device may comprise a light sensor arranged on an outer surface of the wearable electronic device for measuring ambient light and a temperature sensor for measuring the temperature of the user. The wearable electronic device may include any number and types of sensors suitable for collecting data about the user. The measured sensor data from any of the sensors, such as the data of the motion sensor, the optical electronics, the light sensor and the temperature sensor, associated with the user and measured by the wearable electronic device may be considered as raw sensor data. Further the wearable electronic device such as a ring may measure heart rate interbeat intervals and hand movements.

According to an embodiment, the wearable electronic device also typically includes other electronic components configured to collect and analyse sensor data (i.e. raw data). For example, the wearable electronic device may include other electronic components which may include but are not limited to a controller, a microprocessor, a memory and a communication module. The controller is operable to control operation of the sensors for collecting the raw sensor data about the user, for example, data related to the user's movement, heart rate, temperatures and ambient light (to which the user is subjected to). The microprocessor may be operable to process or analyse collected data generated by the sensors. Further, the memory is used for storing one or more of the raw sensor data, the analysed data or the processed data, referred to collectively as the wearable electronic device data. Still further, the wearable electronic device may be operable to perform deep data analysis of any of the wearable electronic device data. It is to be understood that the controller, microprocessor, and memory may include algorithms and other capabilities to perform such deep data analysis. The deep data analysis includes determining or deriving various aspects associated with the user, including but not limited to sleep duration, circadian rhythm, heart-rate-variability, a respiration rate, a sleeping pattern of the user, a hypnogram of the user, various physical provocations or non-provocations the user is subjected to, and user's stress level. The controller, microprocessor, and memory of the wearable device may include algorithms and other capabilities for determining a sleep score and a sleep debt as described below. Moreover, the communication module is typically configured to establish a communication between the wearable electronic device and the mobile communication device.

The mobile communication device is configured to communicate with the wearable electronic device, using the communication module. For example, the mobile communication device may be wirelessly connected to the wearable electronic device by a wireless connection such as a Wi-Fi, Bluetooth and the like. Further, the mobile communication device comprises a computing device which includes but is not limited to a smart phone, a tablet computer, a phablet and a laptop.

In an embodiment, the mobile communication device is configured to collect one or more of the wearable electronic device data, the raw sensor data, the analysed data or the processed data from the wearable electronic device. Further, the mobile communication device is operable to perform deep data analysis of any of the data from the wearable electronic device. It is to be understood that the mobile communication device typically includes required electronic elements, such as a processor and algorithms to perform such deep data analysis.

In an embodiment, the deep data analysis includes determining or deriving various aspects (associated with the user), including but not limited to sleep duration, circadian rhythm, heart-rate-variability, a respiration rate, a sleeping pattern of the user, a hypnogram of the user, various physical provocations or non-provocations the user is subjected to and user's stress level.

The server is configured to communicate with the mobile communication device. For example, the server is communicatively coupled to the mobile communication device through a communication network which can be wired, wireless or a combination thereof. For example, the communication network includes, but is not limited to, Local Area Networks (LANs), Wide Area Networks (WANs), Metropolitan Area Networks (MANs), Wireless LANs (WLANs), Wireless WANs (WWANs), Wireless MANs (WMANs), the Internet, second generation (2G) telecommunication networks, third generation (3G) telecommunication networks, fourth generation (4G) telecommunication networks, and Worldwide Interoperability for Microwave Access (WiMAX) networks.

In an embodiment, the server is configured to collect, through the mobile communication device, one or more of the wearable electronic device data, the raw sensor data, the analysed data or the processed data from the wearable electronic device. Further, the server is configured to perform the deep data analysis of any of the data from the wearable electronic device, in order to determine or derive the various aspects associated with the user, including but not limited to sleep duration, circadian rhythm, heart-rate-variability, a respiration rate, a sleeping pattern of the user, a hypnogram of the user, various physical provocations or non-provocations the user is subjected to, and user's stress level.

In an embodiment, the mobile communication device and the server are configured to operate together to collect one or more of the wearable electronic device data, the raw sensor data, the analysed data or the processed data from the wearable electronic device. Further, the mobile communication device and the server are configured to operate together to perform the deep data analysis of the raw data in order to determine or derive the various aspects associated with the user, including but not limited to sleep duration, circadian rhythm, heart-rate-variability, a respiration rate, a sleeping pattern of the user, a hypnogram of the user, various physical provocations or non-provocations the user is subjected to, and user's stress level. For example, the deep data analysis may be performed partly by the mobile communication device and partly by the server.

The server is operable to collect a first set of information from the user. According to an embodiment, the first set of information comprises physiological performance related information based on an external data input by the user. As mentioned above, the physiological performance related information is mainly derived from the physiological data (or parameters) of the user measured by the wearable electronic device, i.e. heart-rate-variability, a respiration rate, a sleeping pattern of the user, a hypnogram of the user, the user's stress level and the like. However, in the present embodiment, the physiological performance related information is biased or influenced by some external data (or factor), which are different from internal data, such as the biological signals or physiological data associated with the user.

In an embodiment, the external data comprises at least one of travel information, a target set by the user, time zone, calendar, working schedule and holidays. The external data may be received from the user as user input (or feedback) with the help of the mobile communication device. For example, the mobile communication device may be provided with various user interfaces associated with such external data allowing the user to make selection for the external data.

In an embodiment, the travel information comprises information on at least one of past travels, current travels, future travels, time zones, flight times. In one embodiment, the travel information is mainly associated with travel plans in which the user is required to move from one place to another for a substantial distance. In an embodiment, the mobile communication device may include sensors, such as location sensor (for example GPS) to determine the location of the user, i.e. if the user has travelled some distance and moved out of his city/country. Further, the travel may be of such nature that may influence sleep of the user. For example, a travel plan which requires travelling during the night, travelling to different time zones, or travelling in difficult conditions, such as rough terrain. Moreover, the travel plan may include bus journeys or journeys by a water vessel, i.e. for instances when the user travels by bus or ship for a substantial distance, and their times. Additionally, the information of the past travels and the future travels may be such that they may influence the physiological state (parameters or data) of the user when associated with the current travel. In an example, the information of the past travels and the future travels may be comparatively recent (for example few days, a week or a month), such that when the user takes the current travel (or a new travel) the information of the past travels and the future travels may influence the physiological state of the user.

In an embodiment, the server may be operable to determine a current performance level of the user from one or more of a sleep score or a sleep debt, and from one or more of previous physical activity, the user's heart rate, and user's body temperature.

The calculation of the sleep score may utilize two input parameters: EstimatedSleepStages and NightlyActivityClass. The EstimatedSleepStages may include four sleep stages, namely: 1=deep sleep, 2=light sleep, 3=rem sleep, 4=wakefulness. A user may be determined to be in deep sleep when the user exhibits minimal movement and a stable heart rate. The user may be determined to be in light sleep when the heart rate is trending downward and the user exhibits more movement than when in deep sleep but less than the wakefulness state. The user may be determined to be in REM sleep when the user exhibits a variable heart rate and more movement than when in deep sleep but less than the wakefulness state. The user may be determined to be in a wakefulness state when the user exhibits a variable heart rate and more movement than when in light sleep and REM sleep. The EstimatedSleepStages parameter may be determined for a fixed time period, referred to as an Epoch. An exemplary Epoch for the EstimatedSleepStages parameter may be 30 seconds.

The NightlyActivityClass sleep score input parameter may include three activity classes: 1-representing minimal movements indicating a resting state; 2-representing small movements, that is, more movements than movements in activity class 1, but less than activity class 3, and: 3-representing more movements than in activity class 2. A long period in activity class 2, for example, 30 minutes, may be interpreted as a transition to activity class 3. The NightlyActivityClass parameter may be determined for an exemplary Epoch of 60 seconds.

In order to calculate the sleep score, the following values (I-V) may be calculated from the EstimatedSleepStages and NightlyActivityClass input parameters: Total Sleep, Sleep Latency, WakeUpCount, Sleep Efficiency, DeepSleep.

I. Total Sleep (in seconds)=Number of classes "deep," "light" or "REM" in the EstimatedSleepStages*EstimatedSleepStages Epoch length (30 s)

II. Sleep Latency (in seconds)=Number of class "wakefulness" before a first epoch that classifies as a deep, light or REM EstimatedSleepStage * EstimatedSleepStages Epoch length (30 s)

III. WakeUpCount: A WakeUp is marked, after the following two conditions are met in the following order: IF a minimum of 10 minutes of sleep has been observed AND IF a period of at least two minutes of wakefulness is observed. The number of WakeUps during the night is summed, and the last wake-up is excluded.

IV. Sleep Efficiency: Total Sleep (seconds)/(number of elements in the EstimatedSleepStages*EstimatedSleepStages Epoch length (30 s)). The latter corresponds with time spent in bed.

V. DeepSleep=Number of class "deepsleep" sleep stages * EstimatedSleepStages Epoch length (30 s). This corresponds with the total duration of deep sleep.

The above sleep values (I-V) all may have a partial contribution to the sleep score. Each sleep value (I-V) may have a scale that is used to calculate the partial contribution. The partial contributions may be scaled to a value between 0 and 100. For example, I. Total Sleep of 0 minutes may correspond to with a partial score 0, and 540 minutes may correspond with a partial score 100. Between the extreme values of 0 and 100, there may be intermediate points. For example 180 min, 360 min, and 450 min of Total Sleep may correspond with partial contributions of 50, 75 and 85, respectively. Linear interpolation may be performed between the closest two pairs of Total Sleep [0,180,360,450, 540] and the partial contributions [0,50,75,85,100]. For example, 400 min of Total Sleep may be interpolated between points (360,75) and (450,85) as follows (75+(400−360)/(450−360))*(85−75)=79.4.

II. Sleep Latency may also be scaled to between 0 and 100. For example, a Sleep Latency score of 0 may scale to 0 while a Sleep Latency score of 100 may scale to 100, and linear interpolation may be performed between the scores of 0 and 100. One example of a scaled Sleep Latency score may be 90. Sleep Latency may be scaled between Sleep Latency score 0-100 so that Sleep Latencies (presented in minutes) [0, 15,30,60] correspond with Sleep Latency scores [70, 100, 60, 0] and any between these four Sleep Latency values the score is linearly interpolated between the closest two pairs. In practice, falling asleep in 10-20 min gives the best contribution, falling asleep immediately can be a sign of sleep deprivation and if falling asleep takes longer than 30 min the person may have problems in falling asleep that reduce performance (e.g. mental stress).

III. WakeUpCounts may also be scaled to between 0 and 100. As an example, a number of Wakeups of 2 may be scaled to 100 while a number of 30 may be scaled to 0, and linear interpolation may be performed to determine the partial contribution of values between the numbers of 2 and 30. An example of a scaled WakeUpCounts score may be 78. If there is less WakeUpCounts it contributes more positive to performance.

IV. Sleep Efficiency may be scaled to between 0 and 100 such that, for example, 35% corresponds with a partial contribution 0, and a Sleep Efficiency of 95% corresponds with partial contribution of 100. Linear interpolation may be performed between the points of (35%, 0) and (95%, 100) to determine the partial contribution of values of Sleep Efficiency between 35% and 95%. Any Sleep Efficiency value below 35% can be deemed to correspond to partial contribution 0, and any Sleep Efficiency value above 95% corresponds to partial contribution 100. An example of a scaled Sleep Efficiency score may be 68 which would be achieved if Sleep Efficiency value was 76%.

The V. The DeepSleep value may also be scaled to between 0 and 100. For example, a DeepSleep value of 0 min may be scaled to 0, while a DeepSleep value of 80 min or above may be scaled to 100, and linear interpolation may be used to determine the scaled results for DeepSleep values between 0 and 80 min. An example of a scaled DeepSleep value may be 93, which would be achieved if user had accumulated 74 minutes of Deep A weighted sum of the partial contributions may be utilized to determine the sleep score. Exemplary weights could be, for example, 0.50 for I. Total Sleep, 0.10 for II. Sleep Latency, 0.10 for III. WakeUpCount, 0.15 for IV. Sleep Efficiency and 0.15 for V. DeepSleep. For the exemplary weights of 0.50, 0.10, 0.10, 0.15, and 0.15, respectively for the partial contributions of 79.4, 90, 78, 68, and 93, respectively, a sleep score=weight .* partial contributions=0.5*79.4+0.1*90+0.1*78+0.15*68+0.15*93=80.7.

The sleep debt may be based on a Sleep Balance. The Sleep Balance may be determined as a difference between two parameters, namely a weighted average of sleep duration and a personal long-term average sleep duration, during a previous 14 days, where the personal long-term average is required to stay between 7 and 9 hours. If user has been sleeping less than normally and less than 7 hours, sleep balance is negative and user has accumulated sleep debt.

The sleep durations during the previous 14 days may include the cumulative durations of the 1=deep sleep, 2=light sleep, and 3=REM sleep durations for each day, which may be weighted such that the sleep durations of the most recent days may be more heavily weighted. An example of weighting factors (WeightFactors) for an exemplary previous 14 day period, starting from earliest to most recent may be 0.02, 0.05, 0.08, 0.11, 0.15, 0.18, 0.22, 0.30, 0.38, 0.48, 0.55, 0.63, 0.71, and 0.72, respectively.

The personal long-term average sleep duration per day may be computed over the previous 14 days. If the average sleep duration per day is between 420-540 minutes, the average sleep duration per day may be used as the average sleep duration per day if SleepDebt has been accumulated. If the average sleep duration per day<420 min, 420 min may be used as the average sleep duration per day. If the average sleep duration per day>540 min, 540 min may be used as the average sleep duration per day.

When calculating the Sleep Balance WeightFactors:
Sleep_14 days(1:13)=Sleep_14 days(2:14); % shift past nights by one
Sleep_14 days(14)=TotalSleepAmount; % update latest value with total sleep of the past night;
For any missing data of the previous 14 day period the WeightFactors are set to zero, and the Sleep Balance=_sum (WeightFactors) .* (Sleep_14 days–average sleep duration per day))/sum(WeightFactors);

Thus, the sleep debt describes the amount of sleep missing from the average or target set. The average or target can be for example well known 8 hours per night. The sleep debt may be determined by measuring the duration of the sleep during the night and reducing the measured duration from the target amount of the sleep duration. If the value is negative then there is a sleep debt.

The current performance level may be calculated as a weighted sum of measured parameters including at least the sleep score, sleep debt, previous physical activity, user's heart rate, and user's body temperature. Other measured parameters may also be used to calculate the current performance level, including a lowest 10 min average heart rate overnight, an amount of time in bed after the lowest 10 min average heart rate, a total activity of the previous day, a number of minutes of elevated heart rate, e.g. >100 beats/minute, sedentary time over a specified time period, estimated body temperature overnight, age, and gender. The current performance level may be calculated as a weighted sum of the separate effect of each measured parameter including at least the sleep score, sleep debt, previous physical activity, user's heart rate, and user's body temperature on the user's current performance. A weight for each parameter may be calculated by first comparing a value of the parameter to a long term average, for example over 5-30 days, of the parameter of the user, or each parameter may be compared to the average or typical parameter value among a selected human population or group. For example, for a user is a 37 years old male athlete, the selected corresponding human group is male sport people between 35-40 years. Furthermore, for example if the amount of sleep of a user is at least 6.5-8 hours per night, which is enough for the users age group generally defined, and this amount is also more than the long term average of the user, it is determined that the user has slept enough.

The measured parameters may be weighted using a personal sensitivity adjustment based on night to night variations of the parameters for a particular user. For example, if a user's Total Sleep duration varies less than 25 min, 25 min may be used as the personal sensitivity parameter. As another example, if a user's Total Sleep varies more than 45 min, 45 min may be used as the personal sensitivity parameter. In other examples, a user's mean absolute variation of the measured parameters may be used.

As another example, elements R1-R5 of a current performance level, i.e. initial (performance level) readiness may be measured at 45% (very low value) as a weighted sum of a low sleep score the previous night (50 out of 100)which may yield a value of R1 of 40; a wearable electronic device determined sleep debt of 12 hours over the past 2 weeks which may yield a value of R2 of 10; practically no physical activity the previous day (walk-equivalent of activities was 2.0 km while user avg±dev is 6.3±2.2 km, and user preferred health related minimal target level 7.5 km) which may yield a value of R3 of 53; an elevated average HR (heart rate) of 61 bpm (while user avg±dev is 56.5±2.5 bpm) which may yield a value of R4 of 43; and a normal body temperature of 36° C. (while user avg±dev is 36±0.5 degrees Celsius) which may yield a value of R5 of 100. An elevated body temperature may decrease the value of R5, for example a body temperature 37.0° C. would mean R5=25. Also, a lower body temperature may decrease the value of R5, for example a body temperature 35.5° C. would mean R5=75. It is known that men and women may have different body temperatures variations, so this can be taken into account and may result in different scaling rules for men and women.

A weighted sum of the weighted elements may be calculated, for example : R1 by 0.2, R2 by 0.2, R3 by 0.25, R4 by 0.2, and R5 by 0.15, yielding R1*0.2+R2*0.2+R3*0.25+ R4*0.2+R5*0.15=45%, and a separately determined performance level of the user (i.e. new performance level) may be calculated based on additional elements U1-U3 where:
Age: U1 =80,
Feeling: U2=100,
Target: U3=100

Using a weighted average (double weight to Feeling): (U1+U2+U2+U3)/4=95, and a calibration value obtained by scaling 0 to 0.7, 50 to 1.0 and 100 to 1.25, results in (95−50)=45->1+45((1.25−1.00)/50*100))=1.225, and a final readiness=1.225*45%=55%.

In an embodiment, the target set by the user or automatically set target comprises at least one of target stress level, improved sleep, increased activity and definition of personal optimum stress level. For example, the target stress level is a stress level that the user wants to achieve or attain, which preferably includes lower values of stress level. Further, the improved sleep may include increased number of sleep hours or increased quality sleep time, such as time for deep sleep. Furthermore, the increased activity may be associated with physical activity, such as exercise. Moreover, the definition of personal optimum stress level may be a maximum level of stress the user may be subjected to (or may bear).

In an embodiment, the time zone (as the external data) includes information about current time zone where the user is present, for example, a time zone of a place from where the user would initiate the travel. In an embodiment, each region (place) has a different time zone and when a user moves to a different place, the change in the time zone (which is a measure of change in daylight hours) is detected by the light sensor embedded in the wearable electronic device. Further, the calendar includes information of time and dates for past, current and future days, months and years. Furthermore, the working schedule may include information about working hours (for example, day shift or night shift), nature of work (for example, desk job or field job), and the like. Moreover, the holidays include information about calendar holidays, planned and un-planned leaves, and the like.

The server is further operable to calibrate the first set of information based on a set of measurement data from the wearable electronic device. The term "set of measurement data" from the wearable electronic device is present (or real time) physiological data, such as heart-rate-variability, a respiration rate, a sleeping pattern of the user, a hypnogram, the user's stress level and the like, measured by the wearable electronic device, particularly, without any influenced of an external factor. Specifically, the first set of information is calibrated based on the set of measurement data to correlate and optimize the first set of information, such that the calibration yields correct and real time set of information based on the external data input. In other words, the calibration yields real time standardised physiological data of the user based on the external data input by the user. In an example, when the server collects the first set of information from the user, i.e. the physiological performance related information based on an external data (for example the user is travelling from a first place to a second place such as Europe to Japan, on a particular date). The server then calibrates the first set of information based on the set of measurement data (real time data measured by the wearable electronic device) from the user when the user has reached the second place. The phrase calibrating the information or the term calibrated information can refer also to determining a current performance level of the user based on the first set of information and on the set of measurement data from the wearable device.

The server is operable to set the target level of performance of the user. As mentioned above, the term "target level of performance" is associated with a target physiological state of the user (i.e. readiness, capacity, wellness, preparedness or wellbeing of the user) for attending to regular routine jobs or to start a day. For example, a value of the target level of performance should be optimum enough such that the user can efficiently attend to regular routine jobs (or start the day). In an embodiment, the target level of performance may be represented with a numerical value (such as 50% readiness or 80% readiness). Further, the mobile communication device may be provided with various user interfaces associated with such target level of performance allowing the user to make selection for (or set) the target level of performance.

In an embodiment, the target level of performance of the user may be associated with the target set by the user (such as at least one of the target stress level, the improved sleep, the increased activity and the definition of personal optimum stress level). Specifically, the target level of performance depends on the target set by the user. For example, the target level of performance of the user, reaching the second place from the first place, depends on the target set by the user when the user was present in the first place. Further, the target set by the user (such as the target stress level, the improved sleep, the increased activity and the definition of personal optimum stress level) is also dependent on various factors associated with the user, such as circadian rhythm and duration of sleep of the user.

The server is operable to measure circadian rhythm and duration of sleep of the user by the wearable electronic device. In an embodiment, the deep data analysis includes measuring the circadian rhythm and the duration of sleep of the user. Specifically, the wearable electronic device comprises means for measuring the circadian rhythm and the duration of sleep of the user, or the wearable electronic device comprises means for measuring raw data from which circadian rhythm and the duration of sleep of the user can be determined.

In one embodiment, the body temperature of the user is measured by the wearable device (for example a ring) and the time point when the lowest body temperature during the night time, or certain part of the night time, is measured is used as a marking and reference point for a circadian rhythm. These marking points are used for comparing shift of circadian rhythm over days. As wearable devices are measuring distal body temperature, certain selections and signal processing steps can be needed before the body temperature related reference time point can be successfully determined. In the beginning of night, core body temperature drops while distal body temperature rises (for example skin temperature measured by the ring). In one embodiment, this time is excluded from analysis. During REM sleep, temperature regulation is altered. In one embodiment, the temperature data during REM sleep is excluded, or it has a different weight in calculation. Likewise it is inevitable that changes in environment affect skin temperature, for example temperature drops when subject places his/her hand above the blanket instead of keeping it under the blanket. It can be beneficial to exclude these times from analysis and only make the determination based on local maximums, or stable temperature data around them. An alternative is to use a low pass filter to treat these times. Another preferred alternative is to use heart rate data or breathing rate data to fill in the excluded times. The individual model to correlate heart rate/breathing rate and temperature can be done based on the data measured around local maximums, or the values around them that are stable enough.

In an example, the duration of sleep is measured as a time between moment of falling to sleep and moment of waking up. Further, said moments are determined based on at least one of pre-defined changes in heart rate and pre-defined changes in body temperature. For example, the duration of sleep of the user may be derived from the user's hypnogram. Alternatively, the duration of sleep of the user may be measured with the data from the motion sensor (i.e. when the user went to bed and woke up), which should be static or include minute variations (due to no physical provocations). Therefore, based on the data from the motion sensor, how long the user slept can be determined. Otherwise, the data from the motion sensor and the hypnogram may be correlated to measure the duration and quality of sleep.

In an embodiment, the circadian rhythm may be measured using various sensor data. As mentioned above, the wearable electronic device may include a light sensor capable of measuring illumination level as well as colour space. The colour space refers to visible frequencies of the light. For example, if the light sensor detects spectrum that resembles the spectrum of the sun then the light sensor considers the light to be day light. This can be used to determine if the ambient light is from artificial light or natural light. Further, the light sensor can be used to detect illumination conditions during the sleeping time and corrected therewith. Therefore, based on the data from the light sensor, the temperature sensor and the sleeping pattern measurements, a circadian rhythm of the user can be measured. The circadian rhythm may include information such as at around 2 AM the user gets deepest sleep, at 4:30 AM the user has lowest body temperature, at around 6:45 AM the user has sharpest blood pressure, and the like.

According to one embodiment, the target set by the user may also depend on factors, such as sun rhythm. The sun rhythm may include time for the sunrise or sunset that varies with calendar or climate.

The server is operable to compare the measured circadian rhythm, the measured duration of sleep and time information against each other and against a set of rules to determine a separately determined performance level of the user. The circadian rhythm is associated with various time bound physiological aspects of the user, such as sleep quality, body temperature and hormone secretion. Therefore, the measured circadian rhythm, the measured duration of sleep and the time information against each other may be suitably compared. Further, such comparison is performed based on the set of rules. In an example, the set of rules include correlation of the measured circadian rhythm, the measured duration of sleep and the time information against each other. Further, the correlated data for past days and a present day are considered to determine the separately determined performance level for the present day.

The server is operable to compare the separately determined performance level to the target level of performance. Specifically, the separately determined performance level is associated with the performance level determined by comparing the measured circadian rhythm, the measured duration of sleep and the time information against each other based on the set of rules, whereas the target level of performance is set by the user. In an embodiment, the comparison of the separately determined performance level to the target level of performance may include subtraction of values associated therewith. For example, if the separately determined performance level is about 70% readiness and the target level of performance is about 80% readiness, in such instance the comparison thereof may be represented as −10% readiness (as the target level of performance of 80% readiness is not reached). This could be a scenario when the user has reached the second place from the first place, and due to jet lag or sleep deprivation the target level of performance is not reached.

The server is operable to provide an alert and feedback, on the mobile communication device, to the user when the determined performance level is below the target level of performance. In an embodiment, the alert may be a text or a voice message provided on the mobile communication device regarding the determined performance level being below the target level of performance. Further, the feedback comprises instructions to the user on how to achieve the target level of performance. As mentioned above, when the target level of performance is not reached, the user may be provided with feedback to achieve the target level of performance. In an example, if the compared performance level is −10% readiness (i.e. not meeting the target level of performance) the user may be provided with feedbacks, such as "You need three more hours of sleep", "Please sleep by 9 PM", "Please do mild exercise to improve your sleep quality", and the like.

In an embodiment, the server is further operable to store the measured circadian rhythm and the measured duration of sleep. For example, the measured circadian rhythm and the measured duration of sleep may be stored in a database of the server. In an embodiment, the operation and working of the server and the database can be implemented with a dedicated computer system, a cluster of computers and a cloud service. Further, the stored information combined to an input by the user is used in a step of re-calibration of the wearable electronic device. As mentioned above, the input by the user may be associated with the external data, which comprises at least one of travel information, a target set by the user, time zone, calendar, working schedule and holidays. Additionally, the input by the user may be associated with the target set by the user, i.e. at least one of target stress level, improved sleep, increased activity, and definition of personal optimum stress level, presented as input.

According to an embodiment, the input by the user is based on at least one of answer to at least one question, biological data derived from a laboratory test and gender. In an example, the at least one question may include "How are you feeling", "How was your sleep" and "Are you feeling stressed", and their possible answers may be "Feeling fresh" or "Feeling tired", "Good" "Not so good" and "Bad" and "No" and "Yes", respectively. The answer to at least one question may be subjective in nature and primarily based on how the user is feeling about his/her physiological state. Further, in one embodiment, the biological data comprises a level of at least one hormone. For example, the hormone may be at least one of melatonin, oestrogen, progesterone, thyroid, testosterone and the like, which can affect sleep of the user. Therefore, based on the input by the user and the stored information (i.e. the measured circadian rhythm and the duration of sleep) the wearable electronic device may be re-calibrated. The re-calibration of the wearable electronic device may, particularly, include a change in the instruction provided to the user in order to attain the target level of performance.

In an embodiment, based on the achievement and non-achievement of the target level of performance, the instruction may be reused or changed or used with altered degree. For example, if the target level of the performance is achieved, the instruction corresponding to such situation may be saved and may be provided again to the user (upon again achieving the target level of the performance). Further, if the target level of the performance is partially achieved, the instruction may be saved and the same instruction may be provided but with altered (or more aggressive) degree (for example instead of an instruction "You require more sleep" instruction with altered degree "You require more sleep, otherwise you will fall ill" may be provided). Moreover, if the target level of the performance is not achieved, the instruction may be saved by the user, who is provided with a new instruction.

According to an embodiment, as mentioned above, the alert and the feedback provided to the user may be subjective in nature (i.e. would differ from user to user), and differ based on external and internal factors associated with the user. In an embodiment, same measurement data with different user input may lead to different output. For example, there are two users A and B, and the wearable electronic devices associated with each of the users A and B measures equal performance level, i.e. initial readiness measured=45% (very low value). The very low score is determined by the wearable electronic device, which is a weighted sum of the following: low sleep score the previous night (50 out of 100)->R1: 40; the wearable electronic device determined sleep debt of 12 hours over past 2 weeks->R2: 10; practically no physical activity the previous day (walk-equivalent of activities was 2.0 km while user avg±dev is 6.3±2.2 km, and user preferred health related minimal target level 7.5 km)->R3: 53; elevated average HR (heart rate) of 61 bpm (while user avg±dev is 56.5±2.5 bpm)->R4: 43; and yet normal body temperature->R5: 100.

Further, user A is of 45 years of age and has selected an answer to a question "How are you feeling" that he is feeling Very Good (among the options Very good/Good/Bad/Very Bad). The user selects "Working hard" to a question asking about how he is planning to spend the day (Free Day Relaxing/Free Day Active/Working Easy/Working Hard). From these, the system derives a user calibration value of 1.225 (based on a rule, i.e. if Age: U1=80, Feeling: U2=100, Target: U3=100->weighted average (double weight to Feeling)=95, calibration value obtained by scaling 0 to 0.7, 50 to 1.0 and 100 to 1.25). Therefore, user A is provided with the alert, for example compared performance level, such as final readiness=1.225*45%=55%. Further, user A is also provided with the instructions such as to keep workload at a moderate level and how it is beneficial in this condition for his work efficiency and safety to ensure a good night sleep. As user plans to be working hard, the system sets the priority of work related instructions to a higher level which may leave messages related to well-being and general daily performance to be performed on other days.

Additionally, user B is of 55 years of age and selected an answer to a question "How are you feeling" that he is "Feeling Bad". Further, user B selects "Working Easy" to a question asking about how he is planning to spend the day. Based on this, the system derives a user calibration value of 0.977 (based on the rule, i.e. if Age: U1=60, Feeling: U2=25, Target: U3=75->weighted average=46.25). Therefore, user B is provided with the alert that his final readiness is=0.977*45%=44%. Further, user B is also provided with the instructions to keep the workload at an easy level, and how it is necessary in this condition, in order to obtain general well-being and daily performance levels, to go to the bed before 10:30 pm, which is earlier than he normally does. As user B doesn't plan to work hard, the system does not set the priority of work related instructions to a high level, and instead the system gives space to general well-being and daily performance. Further, as the score is below 50%, the system gives actionable suggestions rather than general idea about what is good or what is bad.

In another embodiment, different measurement data and different user input may lead to a same output. In an example, there are two users A and B, and the wearable electronic device associated with each of them measures different performance levels. For example, user A includes an initial readiness measured=45% (very low value). Further, user A is of 45 years of age, and selects an answer to a question "How are you feeling" that he is feeling "Very Good". User A further selects "Working hard" to a question asking about how he is planning to spend the day. Based on these the system derive a user calibration value of 1.225 (with the rule, i.e., if Age: U1=80, Feeling: U2=100, Target: U3=100->weighted average (double weight to Feeling)=95, then calibration value obtained by scaling 0 to 0.75, 50 to 1.0 and 100 to 1.25). Therefore, the system provides the user A with an alert that his compared performance level, such as final readiness=1.225*45%=55%.

On the other hand, user B has performance level, i.e. initial readiness measured=75% (normal value). Further, user B is associated with data, such as the normal sleep score the previous night (70 out of 100)->R1: 40, the wearable electronic device determined sleep debt of 4 hours over past 2 weeks->R2: 60; instructed level of physical activity, yet little above his average (walk-equivalent of activities was 7.5 km while user avg±dev is 6.3±2.2 km)->R3: 70; nightly average HR of 55 bpm (while user avg±dev is 56.5±2.5 bpm)->R4: 90; and normal body temperature->R5: 100. Moreover, the user B is of 65 years of age, and selects an answer to a question "How are you feeling" that he is feeling Very Bad. User B further selects "Free day Relaxing" to a question asking about how he is planning to spend the day. Based on this, the system derives a user calibration value of 0.733 (based on the rule, i.e. if Age: U1=40, Feeling: U2=0, Target: U3=0->weighted average=10). Therefore, the system provides the user B with an alert that his readiness is=0.733*75%=55%. Accordingly, users A and B may be provided with instructions to keep workload at a moderate level and how it is beneficial in this condition for his relaxation, health and social life to ensure a good night sleep. Further, as user B plans to be have a free day, the system sets the priority of work related instructions to a lower level, and in turn, the system sets the priority of messages related to relaxation, health and social life to a higher level.

In one embodiment, the alert and the feedback provided to the user may be based on shifting of circadian rhythm due to travelling. In an example, the system detects 7 hour advance in local time indicating that the user has travelled across the time zones eastwards (e.g. from Denver to London). Further, the system takes into account the person's morningness-eveningness type (calculated by the wearable electronic device from earlier sleep-wake rhythm data, midpoint of the sleep cycle is earlier for morningness-type of person in comparison to eveningness-type of persons, additionally morningness-type of persons are typically more active before noon), indicating that user is a morning type person. The system therefore gives the instructions to the user to stay in a dark room and sleep between 11 PM and 7 AM (local time), avoid ambient light before noon, seek ambient or artificial light after noon, avoid exercise before noon, and eat according to the local meal times. Accordingly, the wearable electronic device measures shifting of the circadian rhythm using following sleep parameters: bedtime, sleep onset time, sleep onset latency, awakening time, sleep midpoint, deep sleep midpoint, REM sleep midpoint. Further, the wearable electronic device modifies the instructions for the following days according to the measured amount of shifting. The wearable electronic device also measures ambient light exposure in order to modify the instructions according to the user's behaviour. If the user may not be able to avoid light exposure before noon, the system guides the user to delay the rhythm instead of advancing during the following days.

In another example, the system detects 11 hours delay in local time indicating that the user has travelled across the time zones westwards (e.g. from Moscow to Los Angeles). The system also takes into account the person's morningness-eveningness type (calculated by the wearable electronic device from earlier sleep-wake rhythm data), indicating that the user is evening type person. Further, the system gives instruction to the user to go to sleep at 11 PM earliest and to stay in bed until 7 AM (local time), seek ambient or artificial light during the afternoon and before 5 PM, avoid exercise before noon, have low-intensity, long-duration exercise between noon and 6 PM, and eat according to the local meal times. Also, the wearable electronic device measures shifting of the circadian rhythm using following sleep parameters: bedtime, sleep onset time, sleep onset latency, awakening time, sleep midpoint, deep sleep midpoint and REM sleep midpoint. Accordingly, the system provides instruction to take into account the measured amount of shift. The wearable electronic device may also measure ambient light exposure in order to modify the instruction according to the user's behaviour.

In another embodiment, the alert and the feedback provided to the user may be based on shifting of the circadian rhythm in advance due to daylight saving time. In an example, the system detects the forthcoming transition from summer time (daylight saving time) to winter time. The system also takes into account the user's habitual wake-up and bedtime (e.g. 5 AM, 9 PM) and morningness-eveningness type (calculated by the wearable electronic device from the earlier sleep-wake rhythm data). In case the user is very morning type person, the system starts to give the user instructions that help the user to adapt to a new external rhythm in advance. The system provides instructions to the user to delay wake-up time and bedtime gradually 30 minutes per day (Day −1: wake up 5:30 AM, to bed: 9:30 PM; transition day (Day 0): wake up 6 AM, bedtime 10 PM) if possible. In addition, the system instructs the user to avoid exercise after 4 PM.

In another example, the system detects the forthcoming transition from winter time to summer time (daylight saving time). The system takes into account the user's habitual wake-up and bedtime (e.g. 8 AM, midnight) and morningness-eveningness type (calculated by the wearable electronic device from the earlier sleep-wake rhythm data), indicating that the user is an evening person. The system accordingly starts to give the user instructions that help the user to adapt to the new external rhythm in advance. The system also instructs the user to advance wake-up time and bedtime gradually 15 minutes per day (when for Day −3 wakeup time is 7:45 AM and bedtime is 11:45 PM; for Day −2 wakeup time is 7:30 AM and bedtime is 11:30 PM; for Day −1 wakeup time is 7:15 AM and bedtime is 11:15 PM; and for transition day (Day0) wakeup time is 7:00 AM and bedtime is 11:00 PM). In addition to facilitate adaptation, the system instructs the user to have high intensity training between 4 PM and 8 PM and avoid all kind of exercise after 8 PM.

According to an embodiment, the system also evaluates consistency of the user input and measured values; points out important input to be asked from user; and general reliability of inputs presented to the user. In an example, the user tells in user input that he is regular by rhythm and morning type of person by temperament; his activity level is on an athletic level; and he is going to have a relaxing free day. Further, the wearable electronic device measure that in previous 2 weeks, deviation of the sleep midpoint been 1:55 (hh:mm) indicating irregular rhythm, and the mean sleep midpoint occurs at 2:00 AM indicating evening type of temperament. In such instance, the system asks how the user is feeling about the daily rhythms over past 2 weeks, if answer is "Very Good", the system expect this person to be irregular by rhythm and evening type of person by temperament, and both findings will affect the message generation. Otherwise, the system gets confirmation that the previous 2 weeks life has been challenging to the physiology of the user.

In another example, the wearable electronic device measures that in previous 1 week, there has been no single day where walk-equivalent distance has exceeded 10 km (for example when the user has been wearing the wearable electronic device during most of the day). In such instance, the system asks if the person is injured or sick and if the user answers "Yes", the system will set the priority of activity related messages to a lower level. Otherwise, the system will not expect the person's activity level be on an athletic level.

In yet another embodiment, the wearable electronic device measures that the user goes in for physical activity equivalent to 25 km of walk or run. In such instance, the system asks the user if his plans changed after planning a relaxing free day and if he answers "No, this is very relaxing to me", the system then set the priority of activity related messages to a higher level and adds the prevalence of messages containing words "fitness", "condition", "strain", "training load", "adrenaline" and "testosterone". In all above cases, in case of inconsistency, the system updates the expected reliability of the user input to a lower level. This will induce a lower weight of the user input related questions in calibration.

According to one embodiment, when the system identifies that the measured data is contrary to the user input, the system starts the discussion with more carefully (give less data at first, give a slight warning of potential disagreement and ask if the user wants to get more information). Further, the system waits longer for the user to answer before providing additional information (e.g. more exact numbers or more lengthy evaluations). Additionally, the system uses more words such as may, can and seems like, and with an introduction, such as "could it be".

In another embodiment, the system also considers data for a period when the wearable electronic device is not worn by the user. For example, the system detects wearable electronic device was not-on-finger on Friday between 10 AM and 11:30 AM. The duration exceeds a pre-set threshold period of e.g. 1 hour, so that the system presents a question to the user about how active the user was during the period, e.g. was he sleeping, very light, moderate or vigorous in terms of work load. However, the user has been playing volleyball, so he selects moderate. Therefore, as a default, the system uses previous answer from the user from the same time spot, the same weekday, whatever is the closest reference time point available.

In an embodiment, the system and the method of the present disclosure may be implemented using a plurality of pseudo codes, and one such example pseudo code includes:

```
nightly_sleep_deep_back_to_average:
    condition: (sleep.night(1).available( ) &&
        sleep.night(2).available( ) &&
        sleep.night(3).available( ) &&
        (sleep.night(3).deep( ) <= sleep.average( ).deep( ) * 0.9) &&
        (sleep.night(2).deep( ) <= sleep.average( ).deep( ) * 0.9) &&
        (sleep.night(1).deep( ) >= sleep.average( ).deep( ) * 0.95))
    priority: 120
    min_interval_days: 7
    TITLE: BACK TO NORMAL SLEEP
    text: 'Your deep sleep amount is back to normal.'
    graph: graph.line(sleep.night(1).deep( ) + " m",
            graph.point(system.wday(3), sleep.night(3).deep( )),
            graph.point(system.wday(2), sleep.night(2).deep( )),
            graph.point(system.wday(1), sleep.night(1).deep( )),
            graph.level("AVG", sleep.average( ).deep( )))
```

The above example of pseudo code is for informing a user, on the mobile communication device, when his average sleep pattern is back to a normal state. The normal state is determined based on longer time measurement of deep sleep, and combination of questions answered from the user to determine what the user regards as normal.

The present disclosure provides a method and a system for providing feedback to a user for improving performance level management thereof. The present disclosure takes into consideration a wide range of both internal and external factors that may affect physiological state or health of the user, which in turn may affect a performance level of the user. For example, the present disclosure takes into consideration travel information, a target set by the user, time zone, calendar, working schedule, and holidays of the user for improving his performance level management. Further, the present disclosure also takes into account user input (such as answers to questions, results of medical tests and gender). Specifically, based upon considering such information, the user may be provided with alerts and feedbacks that enable the user to efficiently improve his performance level management. More specifically, the alerts and feedbacks are based on the information provided by the user himself; therefore the alerts and feedbacks are more accurate and efficient. Therefore, the instruction (i.e. feedbacks) provided to the user when followed by the user, can efficiently improve his performance level. For example, the instruction may help the user to efficiently recover from jetlag and thereby improve his performance level management. Similarly, the instruction may help the user to efficiently recover from other mental or physical stress the user is subjected to, such as work load, inadequate sleep hours and the like.

An Additional Example of Use Case

According to an embodiment, a method for providing feedback to a user for improving performance level management is provided. An example of the performance level management by the user is controlling and following recovery from his daily activities. The daily activities may be physical or mental exercises or for example work related activities causing stress to the user.

The user might want to know his ability to execute longer or more challenging exercises and to manage different kinds of workload better. The user might also want to find out how to recover better from these activities; in practice for example by sleeping longer or going to sleep earlier or waking up earlier or later. The user might also want to know how to manage and get back to balance quickly if something irregular has happened or environmental conditions have changed. One such environmental condition change could be moving from the summertime to the wintertime (daylight saving time) or travelling to another time zone. In addition the user might need to wake up unplanned during the night or wake up earlier than normally.

Based on the example the user uses a measurement device (in this case a ring) on his finger. The measurement device can have a heart rate monitoring and motion sensing means, it can further have an ambient light and an ambient temperature as well skin/body temperature sensing means.

The measurement device can be connected wirelessly to a smartphone. The smartphone may be connected to a web service and a databank over communication network. The measurement device will measure various of parameters. The device can be configured to send data (raw data or processed data) to the smartphone.

According to the present example embodiment, a first set of measured data is collected from the user with the measurement device. The measurement device will measure the first set of measured data at least over one day and night to find out the routines of the user. For example, the first set of measured data can include sleeping time, time to go bed, activities, physical training, heart rate average and minimum and maximum of the heart rate. Further if the user is using the measurement device more than one day and night in the beginning, the measurement device can collect data over many days and do its own analysis of "normal/current" status. Further examples of a first set of measured data would be then normal sleeping times, average time variation to go bed, more detailed heart rate min and max and the variations of heart rate. Additionally activity and training patterns, awakening during night etc. could be added to the first set of measured data.

The smart phone is used to ask or request the user to input a first set of information; such as age, gender, preferences such morningness, eveningness, current subjective status/feeling/balance, improvement needs.

The user's current performance level would be determined based on the first set of information and the first set of measured data from the wearable electronic device. One example of determining the user's current level is to use the first set of information to adjust or calibrate the first set of measured data from the wearable electronic device.

In practice an application in the smart phone could calculate and determine the user's current level. Current level can refer to a circadian rhythm and other parameters that can be described or defined by numerical parameters. Such parameters are: sleeping time (time between going to bed and wake up, i.e. duration of the sleep), sleep time midpoint (the time point for HR min defined for over 1 minute), waking up time, activity time, training time, training level, etc.

The application could also calculate and define normal values to the "average user of the same age and gender based on statistical or other physiological research data". Such normal values could sleeping time for example to 58 years old woman as 8.5 hours sleep between 10.00 PM and 6:30 AM, exercising 2 times per week, each 45 minutes at level of 70% of maximum HR.

A new target level of performance can be derived by the user input (such as setting a new target fitness level by the user) to the smartphone or it can be detected by using a calendar notification or detecting a change of time. The new target level can refer among others for user to adapt to one hour time shift forward or 10 hours time shift backward or improving fitness level by 10%, to match circadian rhythm to the sun rhythm, to improve quality of sleep, or to reach 30 min of moderate intensity physical activity for 3 days in a row.

The measurement device is further used by the user to measure at least one parameter that describes circadian rhythm and at least one parameter that describes amount and/or quality of sleep of the user. The measurement device will send raw data (or pre-processed data) of the measurement to the smartphone. The data can be further sent to a web service.

The smartphone or the web service can calculate, based on at least one parameter, the user's current circadian rhythm and related parameters.

Further, the target level of performance is compared with users' current circadian rhythm and related measured parameters. One example of a measured parameter is the midpoint of the sleep cycle. The midpoint can be defined to be a time period when the heart rate average (for example 1 minute average) is the lowest during the sleep cycle. The application uses the comparison results to derive new corresponding target parameters. For example, a target corresponding parameter could be to change the midpoint of the sleep cycle one hour forward or for example change time to go to sleep 2 hours earlier.

As an example, the application would compare the measured parameter of midpoint of the sleep with the target corresponding parameter. A set of rules related to determining the performance level of the user would be used in the comparison and providing feedback to the user. The application would be configured to show results of the comparison and provide feedback to the user on how to reach target level performance such as changing sleeping patterns.

The user's personal preferences could be used to provide feedback to the user. For example, if there is need for the user to sleep more, the application would propose to sleep later in the morning, because the user goes to bed very early already so there is no point of proposing to go to sleep even earlier. The application can also propose to do physical training earlier in the evening to avoid exercise to disturb the sleep. Other user preferences such as gender, age, fact that user has work stress, or has a baby (baby affects how we interpret awakenings during the night and if day-napping is recommended) can be considered as user input and to be part of the first set of information from the user. Further for example a microphone in the measurement device or in the smartphone can be used if the cause of waking up was a crying baby.

Additionally, the wearable electronic device can be used to make follow up measurements to follow how the user follows the guidance given (=adherence to guidance). As an example, the device measures and application analyses how the user is following the instructions, for example if the user went to the bed according the instruction or not.

Further the device measures and the application analyses how the target and target parameters are reached when the user is following the instructions. For example, when the user went to the bed according the instruction and how the sleep quality has been improved.

The application can further define a parameter how the user follows the instructions. For example, the parameter related to following instructions on time to go bed (0-100%, 0% the user does not follow instruction, 100% the user went to the bed as guided) or a parameter related to make proposed exercises (such as do exercise 2 times per week (50% partly done, 90%—one time done well, second time 80% of the proposed efficiency).

Further the application can determine a parameter that describes user adherence and determine a parameter how well the target is received. The parameters can be used to form user preferences automatically or can be used to provide feedback to the user.

The system will keep record of working instructions. For example the system recognises that the user follows sleeping time instruction very well and it will lead to a good recovery. The system will use that guidance later in similar or another use case. On the other hand, the system can recognise that the user does not follow go to bed time guidance very well, so it does repeat this more than twice.

Further embodiments can include comparing the circadian rhythm to endogenous rhythm or internal bodily rhythm (bodily functions, activity) and to the sun's rhythm (clock and light). Further the measured sleep rhythm based on HRmin or other HR/HRV parameter/s (circadian rhythm), the bodily rhythm (biorhythm of your body) and the sun's time and light rhythm can be compared. Additionally, an ambient light sensor can be used to match circadian rhythm to activities done outdoor/indoor or in front of a screen (sending a blue light).

In additional or alternative embodiments, a method for improving performance level management comprises
- collecting information of the person using measurement device such as heart rate measurement, temperature measurement, movement measurement, electroencephalography (EEG) measurement;
- optionally collecting information of the environment (ambient light, sound, temperature);
- defining rhythms (circadian, bodily, sun);
- calibrating rhythms if needed or possible to do;
- comparing rhythms, define the timing difference between rhythms;
- checking the preferences and targets;
- comparing rhythm timing differences to targets;
- giving feedback and instructions;
- following the next days if the rhythm timing difference is changing/approaching the target or not;
- giving feedback again;
- following the next days if the rhythm timing difference is changing/approaching the target or not
  - if the target is achieved, save the instruction and use it for the next time,
  - if the target is partially achieved, save the instruction and use more aggressive instruction for the next time, and
  - if the target is not achieved, save the instruction and try another instruction for the next time.

In an additional or further aspect, an embodiment of the present disclosure provides a method for providing feedback to a user for improving performance level management. The method comprises steps of:
- collecting a first set of information from the user;
- calibrating the first set of information based on a set of measurement data from a wearable electronic device;
- setting a target level of performance of the user;
- measuring circadian rhythm and duration of sleep of the user by the wearable electronic device;
- comparing the measured circadian rhythm, the measured duration of sleep and time information against each other and against a set of rules to determine the performance level of the user;
- comparing the determined performance level to the target level of performance; and
- providing an alert and feedback to the user when the determined performance level is below the target level of performance, wherein the feedback comprises instructions to the user on how to achieve the target level of performance.

DETAILED DESCRIPTION OF THE DRAWINGS

Referring to FIG. 1, illustrated is a block diagram for a system 100 for providing feedback to a user for improving performance level management thereof, in accordance with an embodiment of the present disclosure. As shown, the system 100 comprises a wearable electronic device 102 configured to be worn by a user 104, a mobile communication device 106 configured to communicate with the wearable electronic device 102, and a server 108 configured to communicate with the mobile communication device 106.

The wearable electronic device 102 is a ring configured to be worn on a finger. The wearable electronic device 102 comprises a set of sensors (not shown). The set of sensors includes an infrared transmitter for measuring heart rate of the user 104, an accelerometer for measuring movements of the user 104, a temperature sensor for measuring body temperature of the user 104 and a light sensor for measuring ambient light and the colour space around the user 104.

As mentioned above, the wearable electronic device 102 is configured to communicate with the mobile communication device 106. For example, the wearable electronic device 102 and the mobile communication device 106 communicate wirelessly through a wireless connection 112, such as Bluetooth and Wi-Fi. The wearable electronic device 102 is configured to communicate with the mobile communication device 106 for communicating the measurement data (or raw data i.e. sensors data) collected by the wearable electronic device 102 from the user.

The mobile communication device 106 is further communicably coupled to the server 108 by a wireless communication network 114, such as LAN, MAN, WAN and the like. Further, the mobile communication device 106 and the server 108 are configured to collect the measurement data collected by the wearable electronic device 102. Moreover, the mobile communication device 106 and the server 108 are configured to perform a deep data analysis of the measurement data in order to find physiological parameters, such as heart rate variability, the user's hypnogram, user's stress level, circadian rhythm, bodily rhythm, sun rhythm and the like, associated with the user 104. Each of the mobile communication device 106 and the server 108 includes a processor 116 and 118, respectively, for performing the deep data analysis. The mobile communication device 106 also includes a location sensor (for example a GPS sensor) to determine the location of the user 104, for example current position, user's 104 movements (travel from one place to another place), and the like. Further, the location sensor data is correlated with the deep data analysis for finding the physiological parameters of user 104 with respect to different places, which may have different time zones.

The server 108 is further communicably coupled to a database 120, which is configured to store the physiological parameters (or processed data, such as heart rate variability, hypnogram, stress level, circadian rhythm, bodily rhythm of the user and sun rhythm). Further, the operation and working of the server 108 and the database 120 can be implemented with a dedicated computer system, a cluster of computers and/or a cloud service. The system 100 accordingly uses the measured and stored physiological parameters for providing feedback to the user 104 for improving performance level management thereof, which is further explained in detail in conjunction with FIG. 2.

Referring now to FIG. 2, illustrated is a block diagram depicting various modules of the server 108 of the system 100 of FIG. 1, in accordance with an embodiment of the present disclosure. Specifically, the server 108 is operable to provide feedback to the user 104 for improving the performance level management thereof.

The server 108 includes the processor 118 and the processor 118 includes various modules, operable to provide such feedbacks that improve the performance level management of the user 104. As shown, the processor 118 includes a data collection module 202, a triggering module 204, a calibration module 206, an analysing module 208 and a feedback module 210. Moreover, the server 108 is communicably coupled to the database 120.

The data collection module 202 is configured to collect a first set of information from the user 104. The first set of information comprises physiological performance related information based on an external data input by the user 104. The physiological performance related information is mainly derived from the physiological data (or parameters) of the user 104 measured by the wearable electronic device 102, i.e. heart-rate-variability, a respiration rate, a sleeping pattern of the user, a hypnogram of the user, the user's stress level, circadian rhythm, bodily rhythm, sun rhythm and the like.

Further, the external data comprises at least one of travel information, a target set by the user 104, time zone, calendar, working schedule and holidays. The travel information comprises information on at least one of past travels, current travels, future travels, the time zones and flight times. The external data is received from the user 104 as user's feedback with the help of mobile communication device 106. For example, the mobile communication device 106 may be provided with various user interfaces associated with such external data allowing the user 104 to make selection for the external data.

The data collection module 202 is configured to collect a set of measurement data (real time set of measurement data) corresponding to the user 104, which is measured by the wearable electronic device 102. The measurement data also includes physiological data measured in real time without the influence of the external data.

Furthermore, the data collection module 202 is configured to collect data input by the user 104 comprising at least one of answer to at least one question, biological data derived from a laboratory test and gender. The biological data includes level of at least one hormone, such as melatonin, oestrogen, progesterone, thyroid, testosterone and the like, which can affect sleep of the user. The answer to at least one question related to wellbeing, sleep pattern, work load, whether a morning person or a night person and the like. For example, the questions are like "How are you feeling" and "how is the work load" and corresponding answers are like "Feeling good" and "Working hard". The questions are presented to the user using various user interfaces (not shown) on the mobile communication device 106. Specifically, the user 104 accesses the questions through an application installed in the mobile communication device 106. Alternatively, the questions may be provided from the server 108 to the mobile communication device 106.

The triggering module 204 is configured to authenticate or check availability of the data collected by the data collection module 202. Specifically, the triggering module 204 is configured to perform a triggering function to authenticate or check the availability of the collected data. For example, a triggering function provides the user 104 with a current heart rate such that the user 104 can see and authenticate that the provided heart rate being correct or incorrect. Also, the triggering function can provide information, such as the heart rate is available for the previous hour or 2-3 minutes (such that average or minimum or maximum of the heart rate can be calculated based thereon). Further, the triggering function can be automatic (i.e. triggered at predefined time) or set by the user 104 (i.e. triggered by the user 104).

The calibration module 206 is configured to calibrate the first set of information based on the set of measurement data from the wearable electronic device 102. Specifically, the first set of information from the user 104, i.e. the physiological performance related information based on the external data (such as, travel information, a target set by the user 104, time zone, calendar, working schedule and holidays) is calibrated (or standardized) with the real time set of measurement data from the user 104 collected from the wearable electronic device 102.

The calibration module 206 is also configured to perform re-calibration of the wearable electronic device 102, which is explained later.

The analysing module 208 is mainly configured to perform the analysis of the data collected by the data collection module 202. Specifically, the analysing module 208 includes a plurality of algorithms for performing the analysis of the data. In an example, the analysing module 208 enables setting a target by the user 104. For example, the analysing module 208 provides an interface on the mobile communication device 106 that allows the user 104 to set a target level of performance. The target level includes at least one of target stress level, improved sleep, increased activity and definition of personal optimum stress level. Further, the analysing module 208 enables rhythm analysis and comparison thereof. For example, the analysing module 208 is configured to compare the measured circadian rhythm, the measured duration of sleep and time information against each other and against a set of rules to determine the performance level of the user 104. Further, the analysing module 208 is configured to compare the determined performance level to the target level of performance. The comparison of the determined performance level and the target level of performance is expressed in terms of percentage of readiness.

The feedback module 210 is configured to provide an alert and a feedback to the user 104 when the determined performance level is below the target level of performance. The alert is provided on the mobile communication device 106 in the form of text or voice message, i.e. the compared performance level, for example 70% of readiness. The feedback includes instructions to the user 104 on how to achieve the target level of performance. For example, the feedback is associated with how to balance biological clock (i.e. to bring changes in the physiological state of the user 104 such that user's circadian rhythm attains balance).

As mentioned above, the calibration module 206 is also configured to perform re-calibration of the wearable electronic device 102. Specifically, the measured circadian rhythm and the measured duration of sleep of the user 104 combined to the input by the user 104 (the at least one of answer to at least one question, biological data derived from a laboratory test and gender) is used in a step of re-calibration. The re-calibration of the wearable electronic device 102, particularly, includes change in the instruction provided to the user in order to attain the target level of performance. For example, if the user 104 indicates in the questions that he does not feel tired and has been sleeping ok but the measurement from the wearable electronic device 102 indicates that there has been very little or no sleep then the instruction is re-calibrated. The database 120 is configured to store the measured circadian rhythm and the measured duration of sleep.

Referring now to FIG. 3, illustrated are steps of a method 300 for providing feedback to a user for improving performance level management thereof, in accordance with an embodiment of the present disclosure. Specifically, those skilled in the art would recognize that the method 300 illustrates steps involved in the operation of the system 100, explained in conjunction with the FIGS. 1-2.

At step 302, a first set of information is collected from the user. At step 304, the first set of information is calibrated based on a set of measurement data from a wearable electronic device. At step 306, a target level of performance of the user is set. At step 308, circadian rhythm and duration of sleep of the user are measured by the wearable electronic device. At step 310, the measured circadian rhythm, the measured duration of sleep and time information are compared against each other and against a set of rules to determine the performance level of the user. At step 312, the determined performance level is compared to the target level of performance. At step 314, an alert and a feedback is provided to the user when the determined performance level is below the target level of performance. The feedback comprises instructions to the user on how to achieve the target level of performance.

The steps 302 to 314 are only illustrative and other alternatives can also be provided where one or more steps are added, one or more steps are removed, or one or more steps are provided in a different sequence without departing from the scope of the claims herein. For example, the method 300 may further comprise a step of storing the measured circadian rhythm and the measured duration of sleep. Further, the method can comprise combining an input by the user with the stored information to re-calibrate the wearable electronic device. Furthermore, in the method 300, the input by the user can be based on at least one of answer to at least one question, biological data derived from a laboratory test and gender. Moreover, in the method 300, the biological data may comprise a level of at least one hormone. Additionally, in the method 300, the duration of sleep can be measured as a time between moment of falling to sleep and moment of waking up, where said moments are determined based on at least one of pre-defined changes in heart rate and pre-defined changes in body temperature. Further, in the method 300, the first set of information can comprise physiological performance related information based on an external data input by the user. Furthermore, in the method 300, the external data can comprise at least one of travel information, a target set by the user, time zone, calendar, working schedule and holidays. Additionally, in the method 300, the travel information can comprise information on at least one of past travels, current travels, future travels, the time zones and flight times. Also, in the method 300, the target set by the user may comprise at least one of target stress level, improved sleep, increased activity, definition of personal optimum stress level.

Referring now to FIG. 4, illustrated are steps of an alternate method 400 for providing feedback to a user for improving performance level management thereof, in accordance with an embodiment of the present disclosure. Specifically, those skilled in the art would recognize that the method 400 illustrates steps involved in the operation of the system 100, explained in conjunction with the FIGS. 1-2.

At step 402, a first set of information is collected from the user. At step 404, a current performance level of the user is determined by: using a wearable device to determine one or more of a sleep score or a sleep debt, and measure one or more of the user's previous physical activity, heart rate, or body temperature; calculating weights for the one or more of the sleep score or a sleep debt, and for the measured one or more of the user's previous physical activity, heart rate, or body temperature; and calculating a weighted sum of the one or more of the weighted sleep score or weighted sleep debt, and the one or more of the weighted user's previous physical activity, weighted heart rate, or weighted body temperature.

At step 406, a target level of performance of the user is set. At step 408, parameters describing a circadian rhythm and a duration of sleep of the user are measured by sensors of the wearable electronic device. At step 410, the at least one parameter that describes a circadian rhythm, the at least one parameter that describes a duration of sleep or sleep cycle of the user, the current performance level, and current time zone information are compared to determine a separately determined performance level of the user. At step 412, the determined performance level is compared to the target level of performance. At step 414, an alert and feedback are provided to the user related to the comparison of the target level of performance and the separately determined performance level.

The steps 402 to 414 are only illustrative and other alternatives can also be provided where one or more steps are added, one or more steps are removed, or one or more steps are provided in a different sequence without departing from the scope of the claims herein. For example, the method 400 may further comprise one or more of a step of storing the measured circadian rhythm and the measured duration of sleep, and a step of receiving user input be based on at least one of answer to at least one question, biological data derived from a laboratory test, and gender. The biological data may comprise a level of at least one hormone. Additionally, in the method 400, the duration of sleep can be measured as a time between a moment of falling to sleep and a moment of waking up, where said moments are determined based on at least one of pre-defined changes in heart rate and pre-defined changes in body temperature. In the method 400, the first set of information can comprise physiological performance related information based on external data input by the user, for example, one or more of travel information, a target set by the user, a time zone, a calendar, a working schedule, and holidays. The travel information can comprise information on at least one of past travels, current travels, future travels, the time zones and flight times. The target set by the user may comprise at least one of target stress level, improved sleep, increased activity, definition of personal optimum stress level.

FIG. 5 is an illustration of an exemplary user interface for providing feedback to the user in a system and using a method incorporating aspects of the disclosed embodiments.

For example, user feedback consists of a graph of numeric data measured from the user, and a written instruction. Figure "day_5" shows five different examples. In the text below are explanations how these messages are formulated or selected among pre-determined candidate messages, or some other potential guidance or feedback is neglected from being shown to the user. The first message (given in the morning) is shown on the bottom, and the latest message (given 9:30 PM) on top of the figure "day_5".

Message 1: "TOO SHORT SLEEP TIME. You need more sleep to recover fully. An earlier bedtime would help you do that."

Observed sleep duration 5 hours 21 minutes is clearly below personal long-term average (e.g. 6 hours 56 minutes), and also below the minimum limit of 7 hours of sleep duration recommended by sleep researchers (e.g. National Sleep Foundation). The graph illustrates how user's last night compares to two earlier nights and his personal average. As an alternative, the graph could also show other target levels determined automatically for the user, or set by user.

User's wake-up time was normal (e.g. within 0-45 minutes), related to his typical day-night rhythm, so it is advisable to advance his bedtime rather than delay wake-up time. Additionally, the set of rules may also take into account that user has a remarkable amount of awake time (e.g. >30 min) detected during the second half of his nights, and less awake time detected during the first half of his nights, measured over the same period of nights where his typical day-night rhythm was determined, meaning that his sleeping performance is worse in the morning than in the evening.

Message 2: "SIGNS OF RECOVERY. Your body responses have recovered well from yesterday's low. However, poor sleep is still limiting your readiness."

Graph shows the readiness score determined for the user over the course of last five days, and user average over longer term. Naturally, the graph could also show other target levels. Sleep duration and circadian rhythm related factors are taken into account in sleep score, which is one parameter used to determine the readiness score. However, readiness score is also taking into account other parameters too, such as users' previous day's physical activity level, physical activity accumulated over e.g. 2 weeks, user's lowest moving average heart rate during the night, users' maximum body temperature during the night, etc. In total, the readiness score exceeds the previous day's level with a clear margin (e.g. >5%), which triggers a positive message about recovery. Additionally, the set of rules may check that the readiness level is below personal long-term average, which triggers a search of the most negative single contributing parameter. In this example case it is very low sleep score, so the set of rules picks it up and poor sleep is mentioned as a limiting factor. Further on, the set or rules may check how long the adverse condition has continued and stronger wording can be selected.

Message 3: "BREATHING EXERCISE. Try a breathing exercise during the afternoon to maintain your performance."

This particular message is suitable in user's current condition (even though in some other occasions relaxation or breathing exercises might not necessarily need to be linked with sleep duration and circadian rhythm and performance level determined thereof). In general, moderate physical activity is recommended for improved sleep. However, because user has already almost reached his target physical activity of 4.7 miles, a target that was determined among other things based on his current activity related performance level, it is not advisable in his condition to recommend more exercise on the same day. So the message related to breathing exercise is shown because the priority of messages that encourage physical activity (or sports or exercise) was set to a lower level.

Message 4: "BREAK UP YOUR SITTING TIME. Try taking short walks to break up your sitting time."

This is basically general guidance to improve health, well-being and performance level, and it can be triggered any time of the day if a prolonged period of sedentary time is determined on the basis of motion sensor data. However, you can easily get fed up with messages that appear too often in your everyday life. Therefore in the set of rules, the priority of this message can be increased if user's readiness level is limited or low. In this case as users' sleep was limited and bedtimes were delayed, the priority is further increased because of the rule that you should especially avoid sedentary time 2-4 hours and physical activity 0-2 hours before circadian rhythm based optimal bedtime to ensure easy sleep onset. As sedentary time in the evenings often include screen time, the guidance could also be related to avoiding screen time 0-3 hours before circadian rhythm based optimal bedtime. Screen time based message can be triggered further if screen time is observed based on ambient light sensor data. More generally, distribution of sedentary time can be used to determine user's day-night cycle, and subsequently, it can serve as a circadian rhythm related parameter (morning type of people sit less before noon).

Message 5: "BEDTIME ALERT. Your optimum bedtime is 11:15 PM. If you want to improve your sleep, try doing some relaxing exercises."

Observed short sleep duration. Observed sleep debt. Observed average bedtime over previous week 12:00 AM. Restless sleep and awakenings observed in second half of the night, hence it is determined that user is a morning type of person, and earlier bedtime is recommended. When advancing of the circadian rhythm, or suggesting earlier bedtime, relaxing exercise before bedtime is recommended in order to help initialise sleep. Alternatively, user's sleep scores could be correlated with determined bedtimes in order to find an optimum zone. This kind of determination could be further improved by taking current sleep needs into account by suggesting added sleep in either evening or morning, for example depending of the determined chronotype of the person.

There are candidate messages ready that all check for conditions that need to be met before any of them can be shown. Since one or more messages could meet their conditions on the same day, a priority for each message may be determined based on how low/high the partial contribution of that factor is, or based on a determined constant priority. The priority may typically be on a continuous scale of arbitrary units, but for clarity, below it is presented as a class variable (very high, high, low). Also the messages may have a time duration and may be prevented from repeating over a certain period of time. In case of the Message 5: "BEDTIME ALERT example, sleep debt and lower than target performance levels may be observed, and a need for longer sleep duration may be clear. The priority may depend on how large a negative sleep balance is observed.

A user can set a preference or reason for wearing the ring, e.g. "improve athletic performance" or "feel more energetic". Different variants may be available for different user preferences. A different variant can be determined for eveningness/morningness chronotypes (different personalities). A restlessness parameter can be determined and if a user is restless, for example, during the second half of the night during more than 50% of the corresponding time, only an earlier go-to-bed time may be recommended. Furthermore, certain parameters are calculated available for the Message Engine, for example median go-to-bed time over the past week (XX:YY AM/PM).

MessageName
  PerformanceLow&SleepDebtHigh&MorningnessType
Condition: Readiness<70 && SleepDebtContritutor<70 && bfTarget 'be more energetic'==1 && RestlessTimeSecondHalf>50% TimeSecondHalf
Priority: IF SleepDebt<30: very high; ELSE IF SleepDebt<50: high; ELSE IF, SleepDebt<70: low, ELSE 0
Message: "Looks like you have been busy lately. Your typical go-to-gedtime during past week has been XX:YY AM/PM. How about finding an earlier bedtime and sticking to it? It would help you get more energetic tomorrow."

A method for providing feedback to a user for improving performance level management may be implemented using a smartphone app that shows feedback so that (after self-reflection) a user will take action and have a higher performance level during the coming days. Collecting a first set of information from the user may be achieved by asking for user inputs (e.g. age, or user-selected target to be more energetic, or morningness/eveningness preference.

Determining a current performance level of the user may be based on the first set of information and on a set of measurement data from a wearable electronic device, and may use the wearable electronic device or an app to calculate a performance level from a sleep duration and an accumulated sleep debt (negative sleep balance), as described above and may also take personal info into account.

A target level of performance may be set for the user, for example, a target performance level may be set by default>=70. Measuring at least one parameter that describes a circadian rhythm and at least one parameter that describes a duration of sleep or sleep cycle of the user may be accomplished by the wearable electronic device. A go-to-bed time may describe a circadian rhythm, which may be measured by the wearable electronic device. A total sleep amount, i.e. duration of sleep, may also be measured by the wearable electronic device.

The method may further include using the target level of performance to determine at least one corresponding parameter that describes the circadian rhythm. Determining that an early bedtime leads to a better performance that exceeds the target level for the user may include making a choice between an earlier bedtime or a later wake-up time that may be determined based on a morningness preference, or the observation of a more restless night during a second half of the night.

The method may further include comparing the measured at least one parameter of the circadian rhythm to a corresponding target based parameter, for example, comparing observed typical go-to-bed times, e.g. 12:00 AM during previous week, to a target based early bedtime, e.g. 10:30 PM-11:00 PM.

The method may still further include providing an alert and feedback to the user related to the determined current performance level and the target level of performance, for example, displaying a message to the user that current performance is low, and it could be improved. The feedback may comprise instructions to the user on how to achieve the target level of performance and the feedback is based on personal preferences of the user. For example, the message may say that the user would be more energetic (which is a personal preference) if he/she went to bed at an earlier time.

Modifications to embodiments of the present disclosure described in the foregoing are possible without departing from the scope of the present disclosure as defined by the accompanying claims. Expressions such as "including", "comprising", "incorporating", "have", "is" used to describe and claim the present disclosure are intended to be construed in a non-exclusive manner, namely allowing for items, components or elements not explicitly described also to be present. Reference to the singular is also to be construed to relate to the plural.

The invention claimed is:

1. A method for providing feedback to a user for improving performance level management, the method comprising:
  collecting a first set of information from the user;
  determining a current performance level of the user by:
    using a wearable electronic device to determine a sleep score and a sleep debt, and measure one or more of a previous physical activity of the user, a heart rate of the user, or a body temperature of the user; and
    calculating a weighted sum of weights for the sleep score, the sleep debt, and the one or more of the previous physical activity, the heart rate, or the body temperature based at least in part on comparing the sleep score, the sleep debt, and the one or more of the previous physical activity, the heart rate, or the body temperature to a respective long term average value;
  setting a target performance level of the user;
  measuring by sensors of the wearable electronic device, a first parameter that describes a circadian rhythm of the user and a second parameter that describes a duration of sleep or a sleep cycle of the user;
  determining a new performance level of the user based on comparing the first parameter, the second parameter, the current performance level, and current time zone information measured over a plurality of days;
  determining a chronotype of the user based at least in part on a midpoint of the sleep cycle, an activity level of the user in a morning, and an activity level of the user in an evening; and
  providing the feedback to the user based on comparing the target performance level and the new performance level, wherein the feedback comprises instructions to the user to change the duration of sleep or the sleep cycle of the user to achieve the target performance level, and wherein the feedback is based on the chronotype of the user.

2. The method according to claim 1, further comprising: determining a moment of falling asleep and a moment of waking up based on at least one of a pre-defined change in heart rate or a pre-defined change in body movement, wherein the second parameter is measured as a time between the moment of falling to sleep and the moment of waking up.

3. The method according to claim 1, wherein the first set of information comprises physiological performance related information based on an external data input by the user.

4. The method according to claim 3, wherein the external data input comprises at least one of travel information, a target set by the user, a time zone, calendar, a working schedule, or one or more holidays.

5. The method according to claim 3, wherein the travel information comprises information for at least one of past travels, current travels, future travels, one or more time zones, or flight times.

6. The method according to claim 3, wherein the target performance level of the user comprises at least one of target stress level, readiness index, improved sleep, increased activity, and definition of personal optimum stress level.

7. The method according to claim 1, further comprising: storing the first parameter and the second parameter.

8. The method according to claim 7, further comprising: recalibrating the wearable electronic device based on the stored first parameter, the stored second parameter, and an input by the user.

9. The method according to claim 8, wherein the input by the user is based on biological data derived from a laboratory test and gender, and the biological data comprises a level of at least one hormone.

10. The method according to claim 1, further comprising:
measuring, after providing the feedback, a third parameter that describes the circadian rhythm of the user and a fourth parameter that describes the duration of sleep or the sleep cycle of the user; and
selectively providing second feedback to the user related to comparing the target performance level and an updated performance level corresponding to the third parameter and the fourth parameter.

11. The method according to claim 1, further comprising: determining a set of parameters that describes user adherence and accuracy of reaching the target performance level, wherein the feedback is based on the set of parameters.

* * * * *